(12) United States Patent
Al-Rafia et al.

(10) Patent No.: US 9,444,060 B2
(45) Date of Patent: Sep. 13, 2016

(54) SYNTHESIS OF NEW SMALL MOLECULES/OLIGOMERS WITH HIGH CONDUCTIVITY AND ABSORPTION FOR OPTOELECTRONIC APPLICATION

(71) Applicant: SABIC GLOBAL TECHNOLOGIES B.V., Bergen op Zoom (NL)

(72) Inventors: S. M. Ibrahim Al-Rafia, Thuwal (SA); Tate C. Hauger, Thuwal (SA); Jillian M. Buriak, Thuwal (SA); Amit Tevtia, Thuwal (SA)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 14/781,872

(22) PCT Filed: Mar. 25, 2015

(86) PCT No.: PCT/IB2015/052215
§ 371 (c)(1),
(2) Date: Oct. 1, 2015

(87) PCT Pub. No.: WO2015/166360
PCT Pub. Date: Nov. 5, 2015

(65) Prior Publication Data
US 2016/0141527 A1    May 19, 2016

Related U.S. Application Data

(60) Provisional application No. 61/985,872, filed on Apr. 29, 2014.

(51) Int. Cl.
*H01L 51/00* (2006.01)
*C07F 7/08* (2006.01)
*C07D 495/04* (2006.01)
*H01L 51/42* (2006.01)

(52) U.S. Cl.
CPC ......... *H01L 51/0094* (2013.01); *C07D 495/04* (2013.01); *C07F 7/0812* (2013.01); *H01L 51/0068* (2013.01); *H01L 51/0071* (2013.01); *H01L 51/0074* (2013.01); *H01L 51/4253* (2013.01); *Y02E 10/549* (2013.01)

(58) Field of Classification Search
CPC ........... H01L 51/0094; H01L 51/4253; C07F 7/0812
USPC ............................................. 257/40; 548/400
See application file for complete search history.

(56) References Cited

U.S. PATENT DOCUMENTS

| | | | |
|---|---|---|---|
| 7,309,876 B2 | 12/2007 | Reichmanis et al. | 257/40 |
| 7,385,221 B1 | 6/2008 | Anthony et al. | 257/40 |
| 8,119,804 B2 | 2/2012 | Brown et al. | 546/49 |
| 8,343,382 B2 | 1/2013 | Bazan et al. | 252/500 |
| 2002/0165215 A1 | 11/2002 | Lam et al. | 514/183 |
| 2007/0287842 A1 | 12/2007 | Skene | 549/50 |
| 2009/0314997 A1 | 12/2009 | Heeney et al. | 252/500 |
| 2010/0117066 A1 | 5/2010 | Heeney et al. | 257/40 |
| 2011/0260114 A1 | 10/2011 | Wu et al. | 252/500 |
| 2013/0062581 A1 | 3/2013 | May et al. | 252/519.3 |
| 2013/0069020 A1 | 3/2013 | May et al. | 252/519.21 |

(Continued)

FOREIGN PATENT DOCUMENTS

| | | |
|---|---|---|
| EP | 2517273 A1 | 6/2011 |
| EP | 2284222 A3 | 1/2012 |

(Continued)

OTHER PUBLICATIONS

Chen et al., "Vacuum-Deposited Small-Molecule Organic Solar Cells with High Power Conversion Efficiencies by Judicious Molecular Design and Device Optimization", *J. Am. Chem. Soc.*, 134(33):13616-13623, 2012.
International Search Report and Written Opinion for PCT/IB2015/052215, mailed Sep. 14, 2015.
Lin et al., "Small molecule semiconductors for high-efficiency organic photovoltaics", *Chem. Soc. Rev.*, 41:4245-4272, 2012.
Gao et al., "Selenophene-Thiophene Block Copolymer Solar Cells with Thermostable Nanostructures", *ACS Nano*, 6(8):7114-7121, 2012.
Su et al., "Organic photovoltaics", *Materials Today*, 15(12):554-562, 2012.
Lehnherr et al., *Organic Letters* 14(14):3660-3663, 2012.

(Continued)

*Primary Examiner* — Kristin Vajda
(74) *Attorney, Agent, or Firm* — Norton Rose Fulbright US LLP

(57) ABSTRACT

Disclosed are semiconducting or conducting organic small molecules and oligomers that contain a central, electron rich, functionalized dihydrodicyclopentylanthracene core (or electron donor core) that is connected to at least one or two comparatively electron deficient monomeric unit or units (or electron acceptor units) that feature group 16 heteroatoms sulfur, selenium or tellurium or combinations thereof. Multiple electron rich cores can be linked together through one or more alkynyl linkages. The small molecules and oligomers can have the following generic structure and can be used in areas such as organic photovoltaic materials:

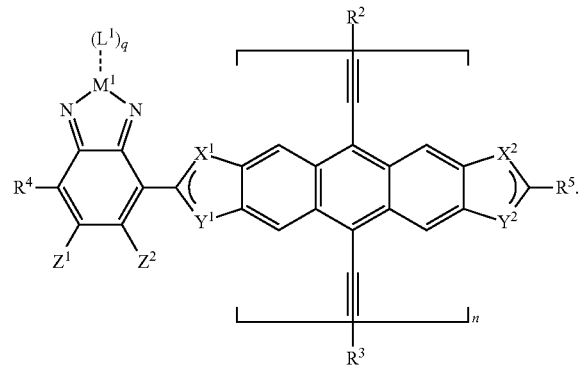

21 Claims, 9 Drawing Sheets

(56) References Cited

U.S. PATENT DOCUMENTS

| | | | |
|---|---|---|---|
| 2013/0146818 A1 | 6/2013 | Wang et al. | 252/500 |
| 2013/0161568 A1 | 6/2013 | Wang et al. | 252/500 |

FOREIGN PATENT DOCUMENTS

| | | |
|---|---|---|
| EP | 2630179 A1 | 4/2012 |
| EP | 2652004 A2 | 6/2012 |
| EP | 2041222 | 12/2012 |
| EP | 2649082 | 1/2015 |
| JP | 2008103464 A | 5/2008 |
| JP | 2010056476 A | 3/2010 |
| JP | 2012519964 A | 8/2012 |
| JP | 2013533911 A | 8/2013 |
| JP | 2013540697 | 11/2013 |
| KR | 2010067386 | 6/2010 |
| KR | 1084685 B1 | 11/2011 |
| KR | 2013066615 A | 6/2013 |
| KR | 2013124347 | 11/2013 |
| TW | 201247735 A | 12/2012 |
| WO | WO2005055248 A2 | 6/2005 |
| WO | WO 2008107089 | 9/2008 |
| WO | WO2011144537 A1 | 11/2011 |
| WO | WO 2012019683 | 2/2012 |
| WO | WO2012160383 A1 | 11/2012 |
| WO | WO 2012164282 | 12/2012 |
| WO | WO 2013098648 | 7/2013 |
| WO | WO2013124686 A1 | 8/2013 |
| WO | WO2013135339 A2 | 9/2013 |
| WO | WO 2013142850 | 9/2013 |

OTHER PUBLICATIONS

Jiang et al., *Macromolecules* 43(15):6361-6367, 2010.
Okamoto et al., *Macromolecules* 41(19):6977-6980, 2008.
Tian et al., *J. Chem. Soc., Perkin Trans. 1* 2:257-261, 1993.
Payne et al., *Organic Letters* 6(19):3325-3328, 2004.
Van der Poll et al., *Advanced Materials* 24:3646-3649, 2012.
Anthony et al., *J. Mater. Chem.* 19:7984-7989, 2009.
Jang et al., *Nanoscale* 5:11094-11101, 2013.
Dickey et al., *Adv. Mater.* 18:1721-1726, 2006.
Mei et al., *J. Am. Chem. Soc.* 135:6724-6746, 2013.
Platt et al., *J. Phys. Chem. C* 113:14006-14014, 2009.
Liu et al., *New J. Chem.* 37:3627-3633, 2013.
Kong et al., *Journal of Polymer Science Part A: Polymer Chemistry* 50:4119-4126, 2012.

SYNTHESIS OF NEW SMALL MOLECULES/OLIGOMERS WITH HIGH CONDUCTIVITY AND ABSORPTION FOR OPTOELECTRONIC APPLICATION

CROSS REFERENCE TO RELATED APPLICATIONS

This Application is a national phase application under 35 U.S.C. §371 of International Application No. PCT/IB2015/052215 filed Mar. 25, 2015, which claims the benefit of U.S. Provisional Patent Application No. 61/985,872 titled "SYNTHESIS OF NEW SMALL MOLECULES/OLIGOMERS WITH HIGH CONDUCTIVITY AND ABSORPTION FOR OPTOELECTRONIC APPLICATION" tiled Apr. 29, 2014. The entire contents of each of the above-referenced patent applications are incorporated into the present application by reference without disclaimer.

BACKGROUND OF THE INVENTION

A. Field of the Invention

The invention generally concerns small molecules and oligomers based on an anthradithiophene core combined with conjugated oligomer side groups comprising Group 16 elements sulfur, selenium, or tellurium, or combinations thereof. These compounds have electron rich and electron deficient regions and can be used in organic electronic applications.

B. Description of Related Art

The search for more efficient and economically viable electronic devices is an ongoing process. This is especially the case for organic electronic applications (e.g., both photovoltaic and non-photovoltaic applications).

While conjugated organic polymers have found widespread use in organic electronic devices including organic light emitting diodes (OLEDs), organic photovoltaics (OPVs) and organic field effect transistors (OFETs), their small molecule/oligomer counterparts have not. One of the reasons for this is that polymers have continuous π-electron systems, and consequent electron-transport properties make them ideal candidates for a variety of electronic devices. Strategic chemical modification of different polymer moieties with varying electron-rich and electron-poor functionalities allows these electron-transporting molecules to be "tuned" for specific applications.

Some of the potential issues with polymeric-based electronic devices, however, are that they are more complicated to make, more difficult to characterize, and more likely to fail (i.e., lack longevity of use) when compared with small-molecule or oligomer-based devices. Despite these issues with polymer-based electronics, the electronics industry continues to implement and develop the use of polymers in electronics to the detriment of small-molecule/oligomer based electronics.

For instance, there are only a handful of small molecules and oligomers that have been demonstrated to lead to moderate-to-high efficiency OPV devices (efficiencies greater than 4%). One of the reasons for this is due to the challenges encountered in designing small molecules and oligomers with both the correct electronic and absorption characteristics and the ability to form nanoscale, phase-segregated, donor-acceptor pairings in the solid state. In terms of the required electronic properties, a suitable band gap is needed for absorption of a broad swath of the solar spectrum, proper alignment of energy levels for charge transfer to the donor or acceptor partner, and suitable (matching) charge carrier mobilities for the balanced transport and extraction of charge from the OPV device.

SUMMARY OF THE INVENTION

The present invention offers a solution to the aforementioned problems associated with both current polymer-based as well as small-molecule and oligomer-based electronics. The solution is premised on a donor-acceptor (D-A) when creating small molecules or oligomers of the present invention, which can be semiconducting or conducting molecules or oligomers. In particular, the small molecules and oligomers of the present invention have been shown to have low band gap semiconducting properties due to the presence of a delocalized π-electron system comprising electron-rich (donor) and electron-deficient (acceptor) units. The donor unit comprises an anthradithiophene core. The acceptor unit utilizes group 16 elements (S, Se, or Te, or any combination or all thereof—e.g., S and S, S and Se, S and Te, Se and Se and Se, Se and Te, or Te and Te, etc.) to allow for improved light absorption properties and enhanced electronic properties, including increased charge carrier mobility. Further, the light absorption properties of the small molecules and oligomers of the present invention can be extended into the ultraviolet and near infrared regions of solar radiation, which allows for increased efficiency as well as fabrication of visibly transparent solar cells. Additional advantages of the small molecules and oligomers of the present invention include: straight forward synthesis; scalable reaction and purification conditions; high degree of solubility in common organic solvents, thereby allowing for efficient solution-based processing during device fabrication; tunable electronic and optical properties via the presence of sulfur, selenium, or tellurium (or any combination or all thereof), which allows for the formation of hypervalent coordination complexes; and photoluminescence properties. Still further, the compounds and oligomers of the present invention can have an overall flat planar structure, which allows for acceptable conjugation lengths.

In one embodiment of the present invention, there is disclosed a compound having the following structure:

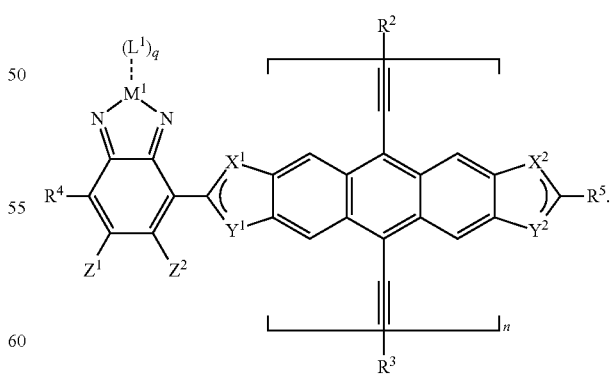

where one of $X^1$ and $Y^1$ is —CH= or =CH— and the other is S, O, $CH_2$ or $NR^1$; one of $X^2$ and $Y^2$ is —CH= or =CH— and the other is S, O, $CH_2$ or $NR^1$; $R^1$ is H or a linear or branched aliphatic group of up to 20 carbon atoms. $R^2$ and $R^3$ can each independently be

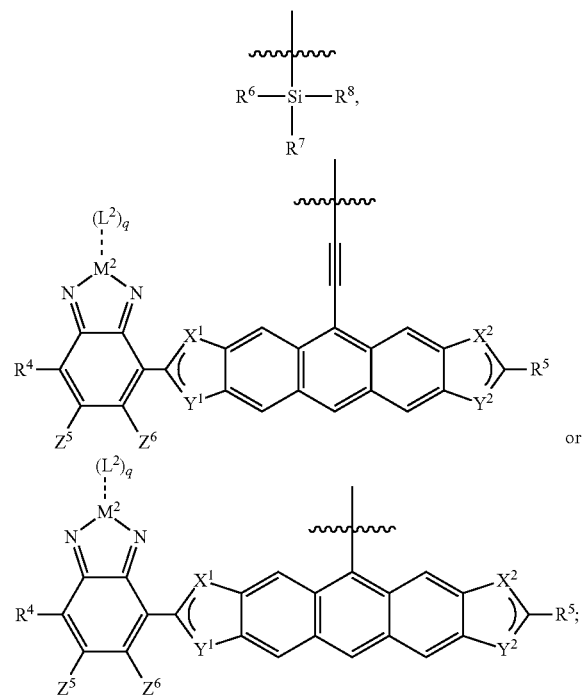

$R^4$ can be

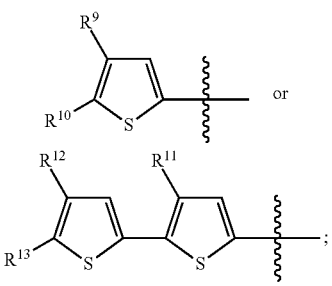

$R^5$ is

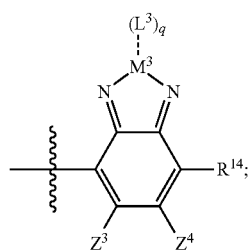

$R^{14}$ can be

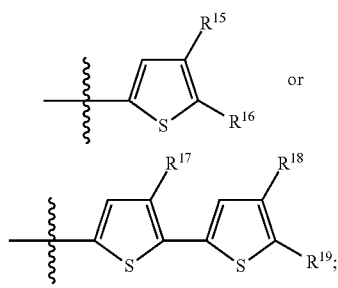

$R^9$, $R^{10}$, $R^{11}$, $R^{12}$, $R^{13}$, $R^{15}$, $R^{16}$, $R^{17}$, $R^{18}$ and $R^{19}$ are each independently H, or a linear, branched or cyclic aliphatic, aryl or heteroaryl group of up to 20 carbon atoms, with the proviso that both of $R^6$ and $R^7$ are not H, both of $R^9$ and $R^{10}$ are not H, both of $R^{12}$ and $R^{13}$ are not H, and both of $R^{15}$ and $R^{16}$ are not H; $M^1$, $M^2$, and $M^3$ are each individually S, Se, or Te; $L_1$, $L_2$, and $L_3$ are each individually a coordination ligand bound to $M^1$, $M^2$, and $M^3$, respectively, through a coordination bond, with q being an integer from 0 to 4; $Z_1$, $Z_2$, $Z_3$, $Z_4$, $Z_5$ and $Z_6$ are each independently H, Cl, Br, F, $NO_2$, CN, $N(R_{20})_2$, $OR_{21}$, $CF_3$, or $C_6H_zE_{6-z}$, or $Z_1$ and $Z_2$ or $Z_3$ and $Z_4$ or $Z_5$ and $Z_6$ are each N and are connected by a metal bridge atom to form, together with the carbon atoms to which they are attached, a 5 member ring system; $R_{20}$ and $R_{21}$ are each independently a linear, branched or cyclic aliphatic, aryl or heteroaryl group of up to 20 carbon atoms; z can be an integer from 0 to 5; and n can be an integer from 0 to 5. By way of explanation, the curved lines spanning the $X^1$, C, and $Y^1$ atoms and the $X^2$, C, and $Y^2$ atoms represent double bonds that can either be present between $X^1$ and C or C and $Y^1$ and between $X^2$ and C or C and $Y^2$. In some particular instances, $M^1$ is S and $M^2$ is S, $M^1$ is S and $M^2$ is Se, or $M^1$ is S and $M^2$ is Te. In other instances, $M^1$ is Se and $M^2$ is Se or $M^1$ is Se and $M^2$ is Te. In still other instances, $M^1$ is Te and $M^2$ is Te. Still further, the number and combination of group 16 elements (e.g., where at least 3 or more such elements are present in a given compound or polymer—$M^3$, $M^4$, $M^5$, etc.) can be selected to achieve a desired result. Such a selection process allows for wider flexibility and tunability in obtaining desired band gaps. In one particular instance, the compound can have the following structure:

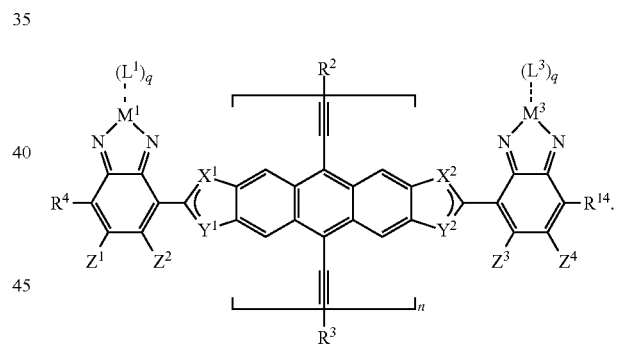

In still another aspect, the compound can have the following structure:

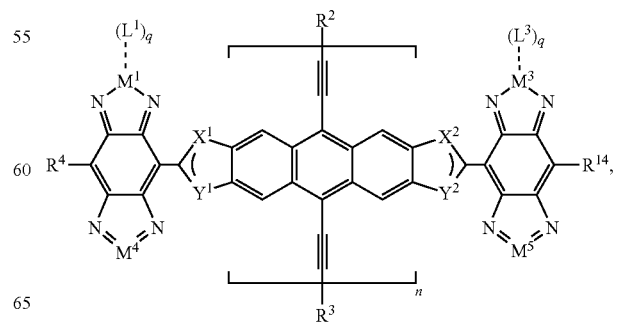

wherein M⁴ is S, Se, or Te, and M⁵ is S, Se, or Te. In another aspect, the compound can have the following structure:
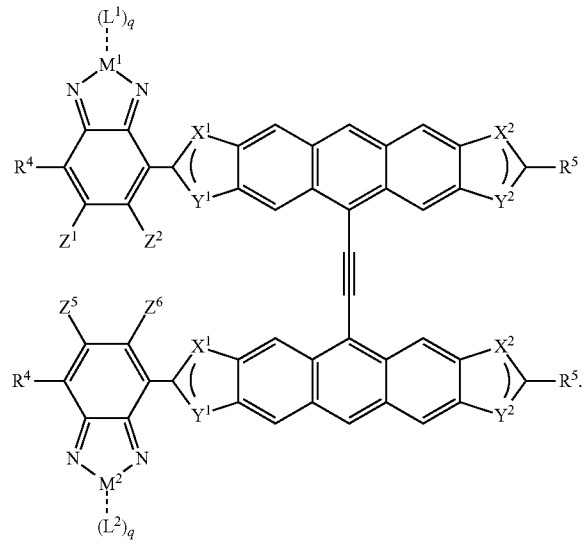
In still another embodiment, the compound can have the following structure:
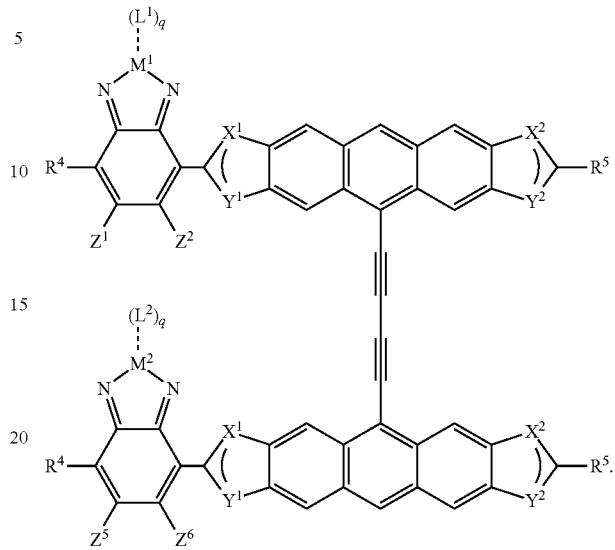
In yet another aspect, the compound can have one of the following structures:
QuIS-S
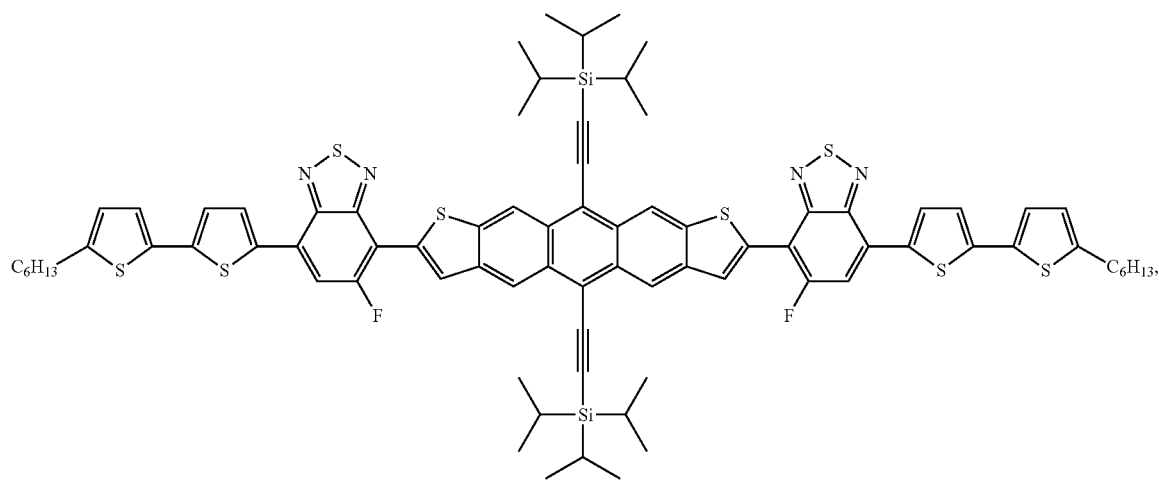
QuIS-Se
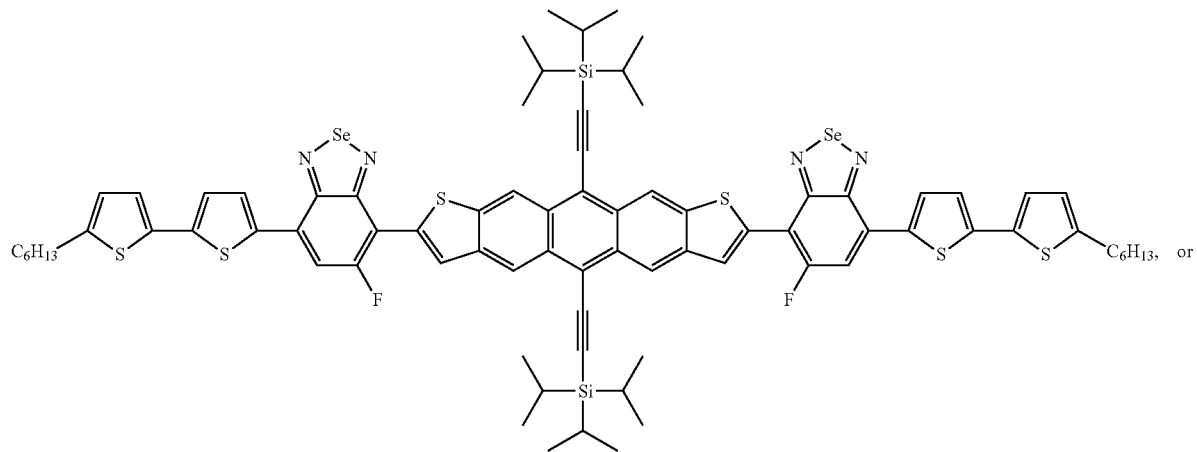
or -continued

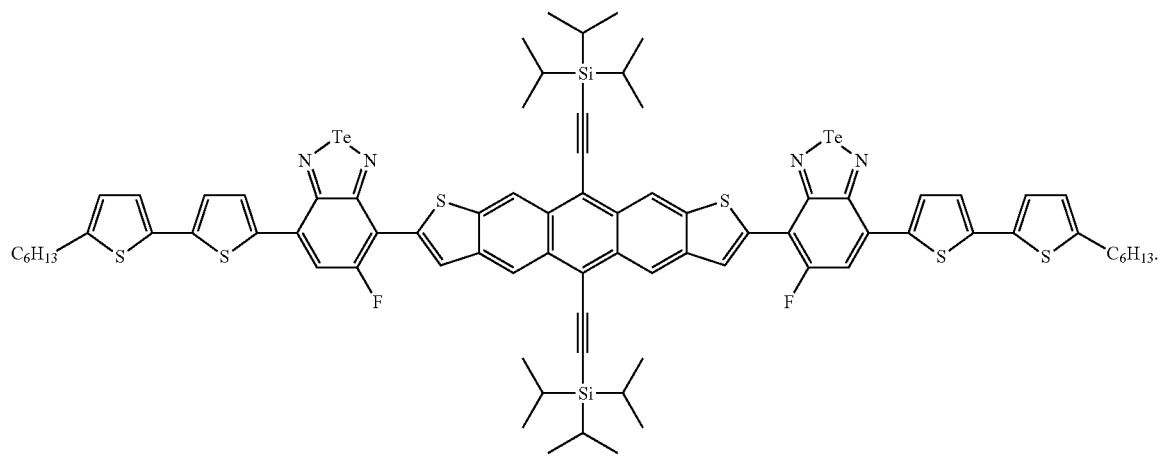

QuIS-Te

Any of the compounds of the present invention can be purified or isolated by techniques known to those of skill in the art (e.g., filtration, precipitation, steam distillation, distillation evaporation, sublimation, centrifugation, decantation, or the like). The purified or isolated compound can be in a dry or powdered form or can be stored within a liquid. The produced compound can be further modified with a dopant so as to enhance its p-type or n-type properties. The produced compounds can be conductive or semi-conductive compounds and can be used in such electronic applications and devices.

In another embodiment of the present invention, the compounds (e.g., small molecules and oligomers) of the present invention can be used in electronic applications. These compounds can be used in an active layer of an electronic device. The active layer can be an organic or hybrid semiconducting or conducting layer. The device can include a substrate, the photoactive layer, and at least two electrodes, one of which is transparent, wherein at least a portion or all of the photoactive layer is disposed between said electrodes. The transparent electrode can be a cathode and the other electrode can be an anode. Alternatively, the transparent electrode can be an anode and the other electrode can be a cathode. In some instances both of the aforementioned electrodes can be transparent. In other instances, one of the electrodes can be transparent while the other is non-transparent (e.g., opaque) or reflective, such that it can reflect electromagnetic radiation such as ultraviolet light or visible light or sun light. Still further, the substrate can be opaque, reflective, or transparent. In particular instances, the electronic device can be a photovoltaic cell or can include a photovoltaic cell. Said cell may not include an electrolyte. The photovoltaic cell can be designed such that it is a single active layer or bi-layer photovoltaic cell. A bulk-heterojunction layer can be produced by using the compounds of the present invention alone or in combination with known small molecule, oligomers, or polymers, or combinations thereof. The photovoltaic cell can be included in an organic electronic device. Examples of such devices include organic light-emitting diodes (OLEDs) (e.g., polymeric organic light-emitting diodes (PLEDs), small-molecule organic light-emitting diodes (SM-OLEDs), organic integrated circuits (O-ICs), organic field effect transistors (OFETs), organic thin film transistors (OTFTs), organic solar cell (O-SCs), and organic laser diodes (O-lasers).

Also disclosed is a process for applying an organic or hybrid semiconducting or conducting layer on a substrate or an electrode, wherein the semiconducting or conducting layer comprises any one of the compounds of the present invention. The process can include disposing said semiconducting or conducting layer on said substrate or said electrode. The semiconducting layer can be photoactive. The conducting layer can be photoactive. The substrate can be rigid or flexible. The substrate can include an electrode and the photoactive layer can be disposed on said electrode. The substrate may not include an electrode, and the photoactive layer can be disposed on the substrate. The substrate can include an electrode and the photoactive layer can be disposed on the substrate or the electrode or onto both. Deposition of said layer can be by spray coating, ultra sonic spray coating, roll-to-roll coating, drop casting, dip coating, Mayer rod coating, gravure coating, slot die coating, doctor blade coating, spin coating, meniscus coating, transfer printing, ink jet printing, offset printing or screen printing process. Alternatively, deposition of said layer can be by vacuum deposition or organic vapor phase deposition (OVPD), solution precipitation, organic molecular beam deposition, or vacuum thermal evaporation (VTE). In preferred aspects, vacuum deposition is vacuum thermal deposition.

A linear aliphatic group is a substituted or unsubstituted, saturated hydrocarbon with no tertiary or quaternary carbons. Aliphatic group substituents include, but are not limited to halogen, hydroxyl, alkyoxy, haloalkyl, haloalkoxy, carboxylic acid, ester, amine, amide, nitrile, acyl, thiol and thioether.

A branched aliphatic group is a substituted or unsubstituted, saturated hydrocarbon that includes at least one tertiary and/or quaternary carbon. Branched aliphatic group substituents include, but are not limited to alkyl, halogen, hydroxyl, alkyoxy, haloalkyl, haloalkoxy, carboxylic acid, ester, amine, amide, nitrile, acyl, thiol and thioether.

A cyclic aliphatic group is a substituted or unsubstituted, saturated, hydrocarbon that includes at least one ring in its structure. Polycyclic aliphatic groups may include fused, e.g., decalin, and/or spiro, e.g., spiro[5.5]undecane, polycyclic groups. Cyclic aliphatic group substituents include, but are not limited to alkyl, halogen, hydroxyl, alkyoxy, haloalkyl, haloalkoxy, carboxylic acid, ester, amine, amide, nitrile, acyl, thiol and thioether.

An aryl group is a substituted or unsubstituted, mono- or polycyclic hydrocarbon with alternating single and double bonds within each ring structure. Aryl group substituents include, but are not limited to alkyl, halogen, hydroxyl, alkyoxy, haloalkyl, haloalkoxy, carboxylic acid, ester, amine, amide, nitrile, acyl, thiol and thioether.

A heteroaryl group is a mono- or polycyclic hydrocarbon with alternating single and double bonds within each ring structure, and at least one atom within at least one ring is not carbon. Heteroaryl group substituents include, but are not limited to alkyl, halogen, hydroxyl, alkyoxy, haloalkyl, haloalkoxy, carboxylic acid, ester, amine, amide, nitrile, acyl, thiol and thioether.

An aromatic group is a substituted or unsubstituted, mono- or polycyclic hydrocarbon with alternating single and double bonds within each ring structure. Aromatic group substituents include, but are not limited to alkyl, halogen, hydroxyl, alkyoxy, haloalkyl, haloalkoxy, carboxylic acid, ester, amine, amide, nitrile, acyl, thiol and thioether.

A hetero-aromatic group is a mono- or polycyclic hydrocarbon with alternating single and double bonds within each ring structure, and at least one atom within at least one ring is not carbon. Hetero-aromatic group substituents include, but are not limited to alkyl, halogen, hydroxyl, alkyoxy, haloalkyl, haloalkoxy, carboxylic acid, ester, amine, amide, nitrile, acyl, thiol and thioether.

An alkyl group is linear or branched, substituted or unsubstituted, saturated hydrocarbon. Alkyl group substituents may include, but are not limited to alkyl, halogen, hydroxyl, alkyoxy, haloalkyl, haloalkoxy, carboxylic acid, ester, amine, amide, nitrile, acyl, thiol and thioether.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The use of the word "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compounds and related processes of making and using said compounds, the photoactive layers, the photovoltaic cells, and the organic electronic devices of the present invention can "comprise," "consist essentially of," or "consist of" particular ingredients, components, compounds, compositions, etc. disclosed throughout the specification. With respect to the transitional phase "consisting essentially of," in one non-limiting aspect, a basic and novel characteristic of the aforesaid compounds are their light absorption and charge carrier mobility properties.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

DETAILED DESCRIPTION OF THE INVENTION

Figure 1:
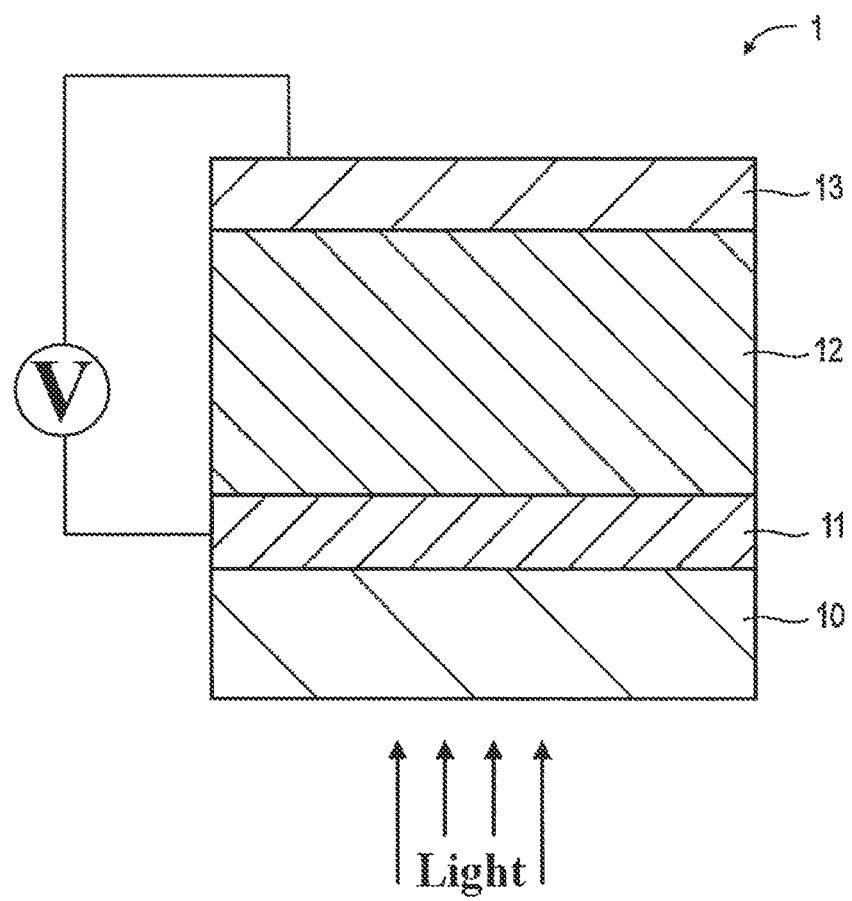
FIG. 1: Illustration of an organic photovoltaic cell incorporating the small molecules or oligomers or polymers or all types of the present invention.

As explained above, the present invention offers a solution to the problems associated with current small molecules and oligomers that are used in organic electronic devices. The solution resides in the creation of small molecules or oligomers that have low band gap semiconducting properties due to the presence of a delocalized π-electron system that has an electron rich (donor) anthradithiophene core and an electron-deficient (acceptor) unit having group 16 elements such as sulfur, selenium, or tellurium. The compounds and oligomers have good light absorption and electronic properties, including increased charge carrier mobility.

These and other non-limiting aspects of the present invention are discussed in detail in the following sections.

A. Semi-Conductive or Conductive Compounds

The compounds of the present invention can be prepared as small molecules or oligomers that contain a central electron rich monomeric unit (or electron donor unit) or units in instances where oligomers or polymers are concerned that have an electron rich monomeric unit that is connected to at least one or two comparatively electron deficient monomeric unit or units (or electron acceptor units) that feature group 16 heteroatoms of sulfur, selenium, or tellurium or combinations thereof. The compounds and oligomers can be semi-conductive or conductive. Larger units are also contemplated and can be prepared to achieve a desired compound or oligomer. Further each small molecule or oligomer can be terminated with a thiophene capping unit. In addition to the compounds prepared in the Examples, the following provides non-limiting schemes that can be used to prepare small molecules and oligomers of the present invention. Notably, the small molecules and oligomers can be modified with additional non-functional or functional groups as desired. Further the small molecules and oligomers can be soluble in common organic solvents, examples of which are provided below, and stable for extended periods of time under ambient conditions.

1. Electron Acceptor Units

The following reaction scheme 1 illustrates a non-limiting process to make monomeric electron acceptor units that can be used with the small molecules and oligomers of the present invention:

Reaction Scheme 1

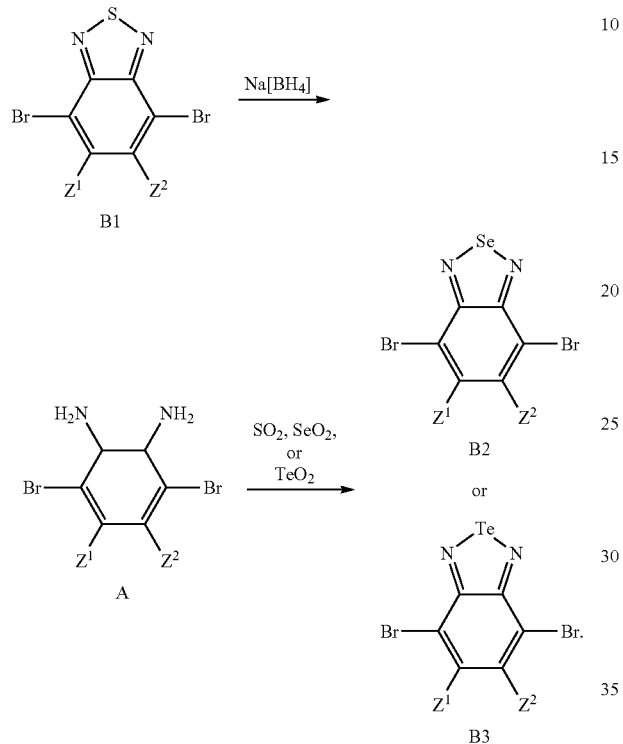

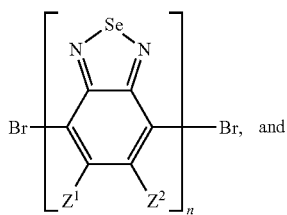

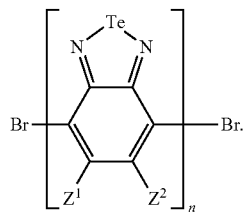

Referring to Scheme 1, excess (5-10) of equivalent Na[BH$_4$] can be used to synthesize compound A. In preferred embodiments, compounds B1, B2, B3 are attached directly to an electron donor unit by using the processes described throughout this specification or processes known to those of ordinary skill in the art. However, each of compounds B1, B2, and B3 can be linked together to create small oligomers (e.g., the oligomers contain up to 5 monomeric units (i.e., n can be an integer of 1, 2, 3, 4, or 5 or more). This oligomerization step can be performed by using well established coupling reactions such as Suzuki coupling where compounds B1, B2, and/or B3 are coupled with a boronic acid or boronic ester containing moiety. The desired coupling reaction can also be carried out using Stille coupling when compounds B1, B2, and/or B3 are reacted with a tin containing organic moiety to produce compounds B4, B5, and B6

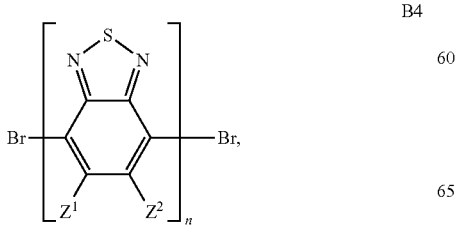

The produced B1, B2, B3, B4, B5, and B6 compounds can then be used in reaction scheme 2 to obtain thiophene end units or caps:

Reaction Scheme 2

B1, B2, B3, B4, B5, or B6  +

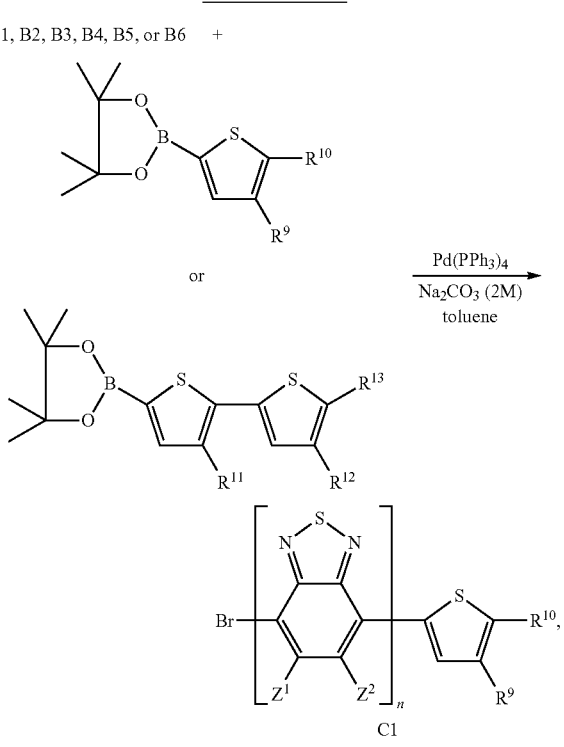

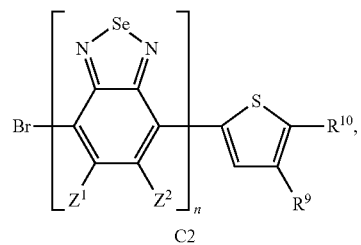

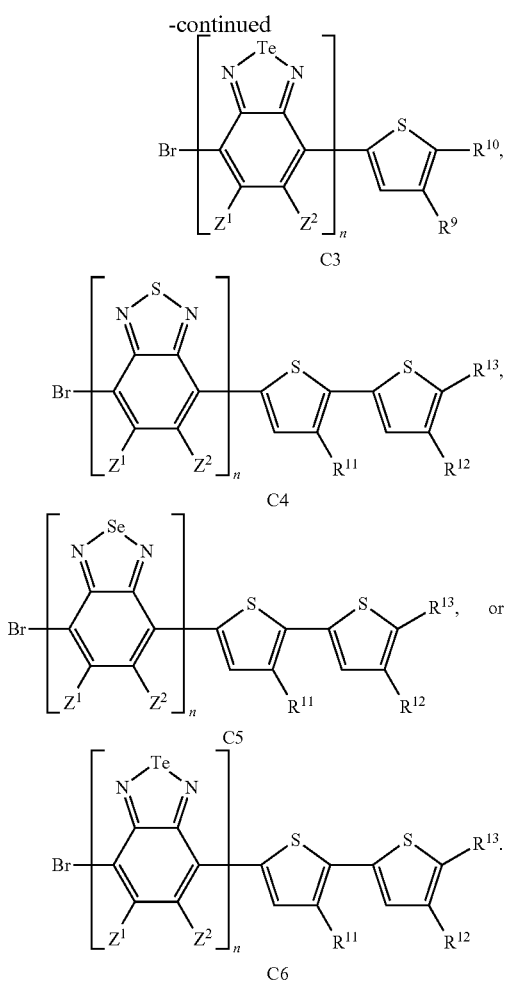

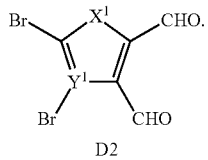

The $X^1$ and $Y^1$ groups can be switched with the aforementioned $X^2$ and $Y^2$ to obtain compounds D3 and D4, respectively, with D3 having a single Br group and D4 having two Br groups. Additionally, the $Br_2$ and acetic acid can be used in excess of the stoichiometric amount to synthesize compounds D1, D2, D3, and D4. Any one of, or any combination of, D1, D2, D3, and D4, can then be reacted with 1,4-cyclohexanedione and an ethanol solution of KOH under room temperature conditions (20 to 25° C.) and mixed until the reaction is complete (e.g., about 2 to 4 hours). In preferred embodiments, D1 and D3 can be used. The amounts of D1, D2, D3, D4, 1,4-cyclohexanedione, and the ethanol solution of KOH can be varied as needed to produce a desired amount of the following compound D5. This is illustrated in reaction scheme 4:

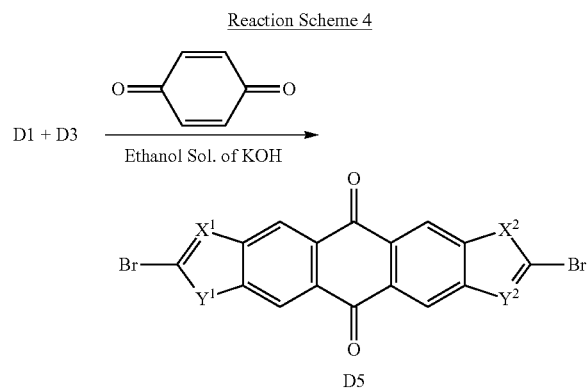

Referring to scheme 2, the reaction can be performed under Suzuki coupling reaction conditions and the catalyst Pd(PPh$_3$)$_4$, solvent (toluene) and activator (Na$_2$CO$_3$) can vary depending on the reaction. In some cases, different sets of catalysts, solvents and activators can be used. Also the percentage of product formation can change by modifying these parameters. Alternatively, the small molecule or oligomer can be terminated with an aromatic, hetero-aromatic, or alkyl functional group rather than with a thiophene capping unit. The $R^9$, $R^{10}$, $R^{11}$, $R^{12}$, $R^{13}$, and $Z^1$ and $Z^2$ groups are defined above in the summary of the invention section and in the claims, the definitions of which are incorporated into this section by reference. The C1, C2, C3, C4, C5, and C6 compounds can then be covalently linked to an electron donor unit.

2. Electron Donor Units

Reaction scheme 3 provides a non-limiting process to make an electron donor unit that can be used with the molecules and oligomers of the present invention.

Alternatively, compound D6 can be prepared according to the following reaction scheme 5:

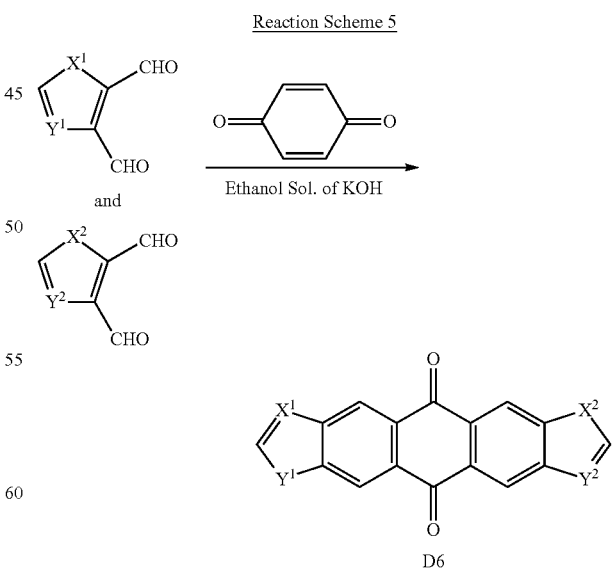

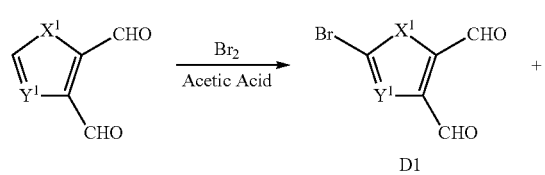

Either one of D5 or D6 can be used in the following reaction schemes 6 and 7, respectively, to produce compounds D7 and D8:

Reaction Scheme 6

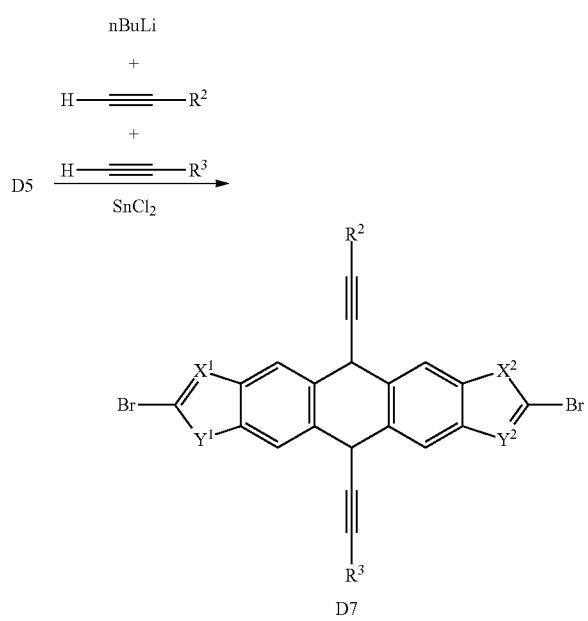

and

Reaction Scheme 8

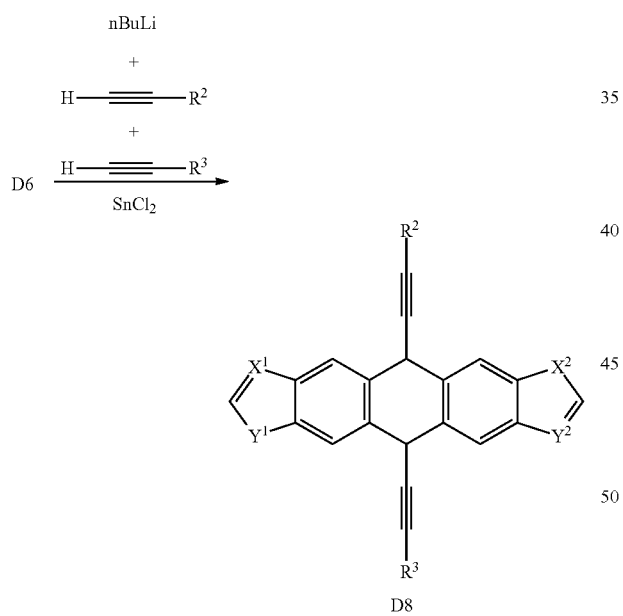

Referring to reaction schemes 6 and 7, the n-BuLi can be added to the $R^2/R^3$ substituted acetylene compound and heated (e.g., about 60° C.) for a sufficient period of time (e.g., about 1 hour) to form a reaction mixture. Subsequently, the mixture can be cooled to room temperature and compound D5 or D6 can be added under a nitrogen stream and heated (e.g., about 60° C.) for a sufficient period of time (e.g., about 12 hours). Subsequently, the reaction mixture can be cooled to room temperature and a solution of stannyl chloride hydrate in a 10% HCl solution can be added. The reaction mixture can then be heated (e.g., about 60° C.) for a sufficient period of time (e.g., about 2 hours) to produce compounds D7 and D8, respectively. The compounds can be purified via filtration through a silica gel flask column using hexane as an eluent.

Additionally, either of compounds D7 and D8 can be further used to produce compounds D9 and D10, respectively under the following reaction scheme 8 (notably, D7 and D8 are identical to D9 and D10, respectively, when n is 1):

Reaction Scheme 8

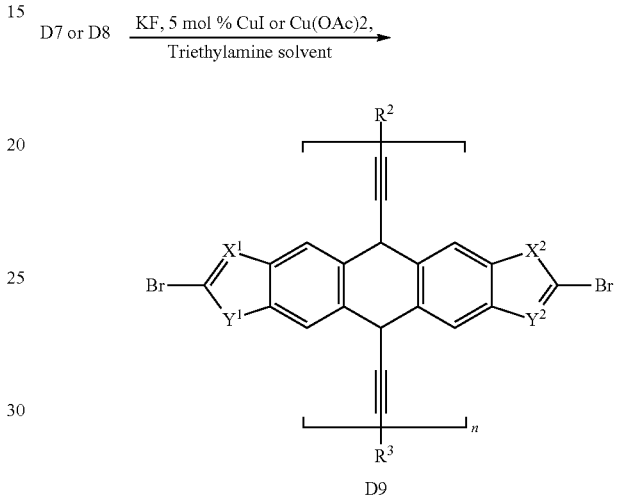

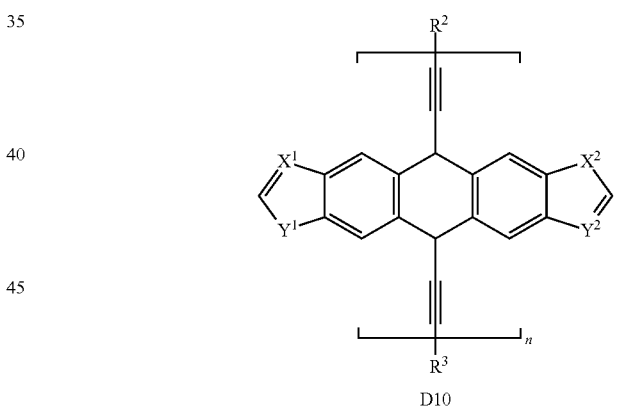

The above reaction can be performed by deprotecting and removing $R^2$ and $R^3$ using tetrabutyl ammonium fluoride or CsF or KF to form alkyne functionality, followed by Cu catalyzed coupling reaction. The general non-limiting reaction conditions can include: 5 mol % CuI or Cu(OAc)2, triethylamine solvent, $O_2$. Both steps can be performed separately or in one pot.

Compounds D7, D8, D9, or D10 can then be placed in THF and reacted in the presence of lithium di-isopropyl amide (LDA) at a sufficiently cold temperature (e.g., about −78° C.) for a sufficient period of time (e.g., about 1 hour) to produce a reaction mixture. Subsequently, trimethyltin chloride can be added to the reaction mixture at approximately the same temperature and then gradually warmed to room temperature under continuous stirring for a sufficient period of time (e.g., about 12 hours) to obtain compound D11, where n is from 1 to 5. Reaction scheme 9 illustrates this:

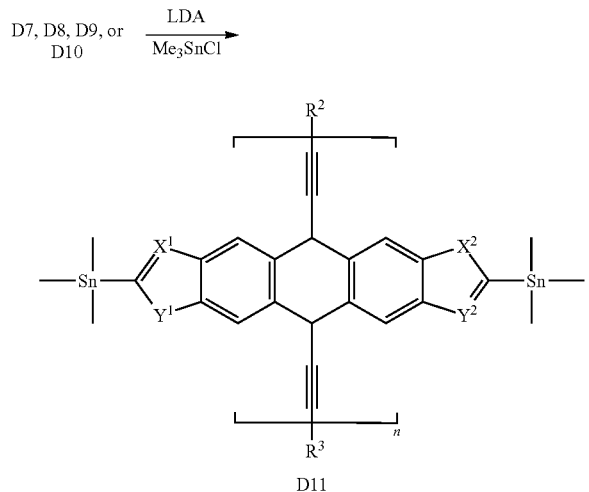

Reaction Scheme 9

D11

3. Attachment of the Electron Acceptor and Donor Units

Each of the produced electron acceptor and donor units can then be covalently linked together to form a variety of compounds (i.e., small molecules and oligomers) of the present invention. The covalent linkage can be made by reacting the bromine group on the electron donor unit with the trimethyltin group(s) present on the electron donor unit by using the following reaction conditions. A microwave glass tube can be charged with compound C (e.g., C1, C2, C3, C4, C5, or C6 or combinations thereof), compound D (e.g., D11), Pd(PPh$_3$)$_4$ and dry THF. The glass tube can be sealed with a Teflon® cap and stirred at room temperature following by heating the reaction mixture in a microwave to form covalent links between the electron acceptor (C) and electron donor (D) units. This is illustrated in reaction scheme 10:

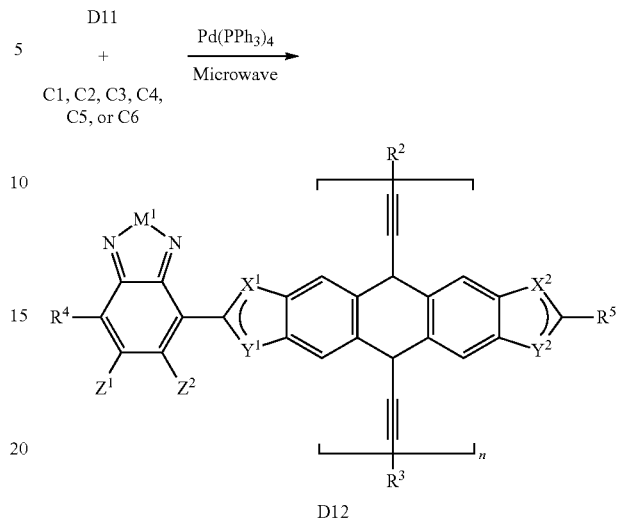

Reaction Scheme 10

D12

As noted in a non-limiting aspect, the stirring step can be for a sufficient period of time (e.g., about 15 minutes) at room temperature conditions (20 to 25° C.), and the heating step can be performed in stages (e.g., about 100° C. for 2 minutes, followed by 125° C. for 2 minutes, followed by 140° C. for 10 minutes, followed by 150° C. for 10 minutes, followed by 160° C. for 20 minutes, followed by 170° C. for 30 minutes.).

Additionally, coordination complexes can be formed between the sulfur, selenium and tellurium atoms (i.e., M groups) on the compounds of the present invention with a coordination ligand, such as Cl, Br, I, a linear, branched or cyclic aliphatic, aryl or heteroaryl group of up to 20 carbon atoms. The formation of these coordination complexes can be used to increase the charge carrier mobility of the compounds of the present invention and further enhance their tunability for use in electronic devices.

The following includes non-limiting compounds of the present invention that can be made by utilizing the aforesaid reaction schemes, in which the various M, R, X, Y, and n groups and integers are those that have been previously defined in the summary of the invention section and claims of the specification:

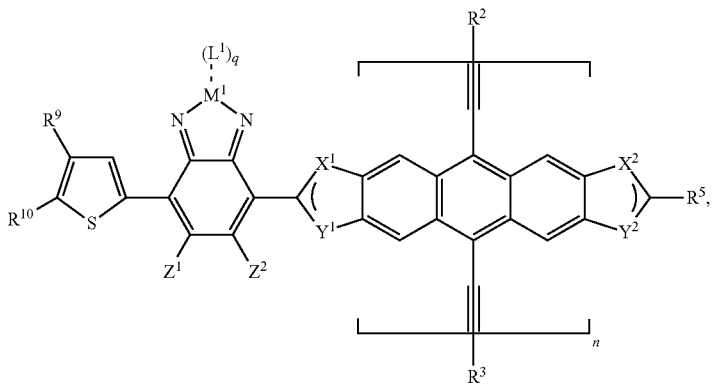

-continued
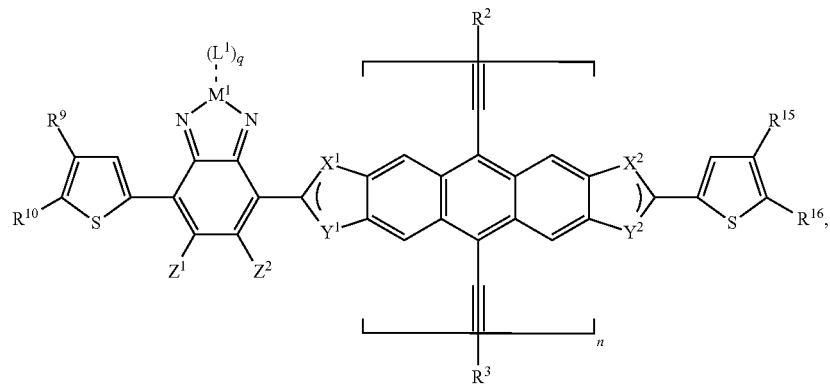
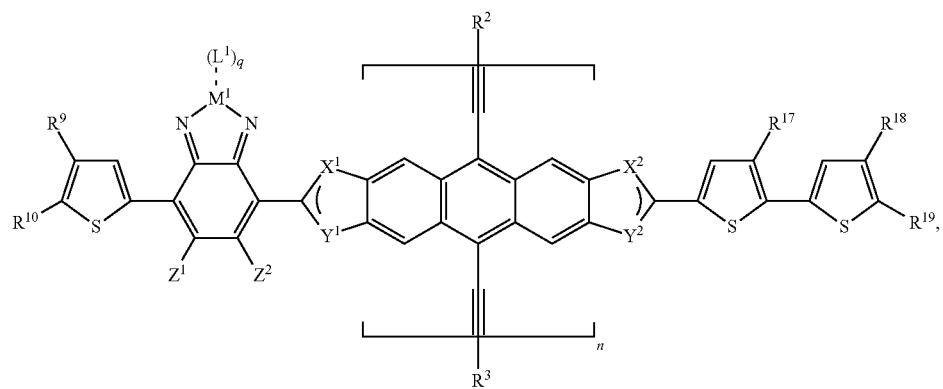
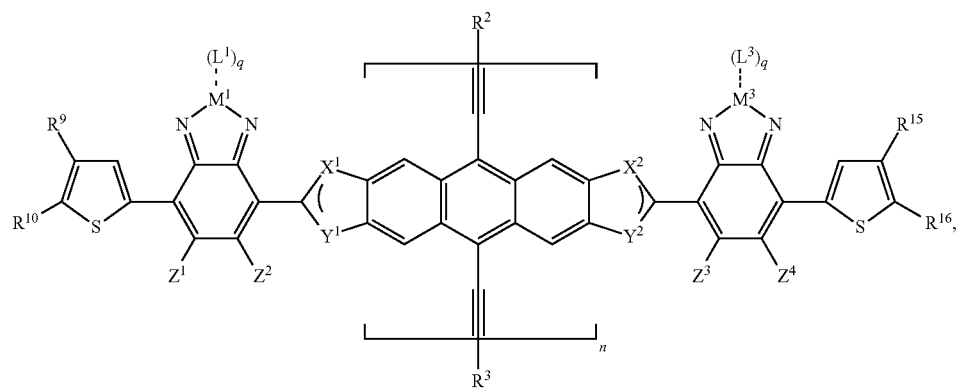
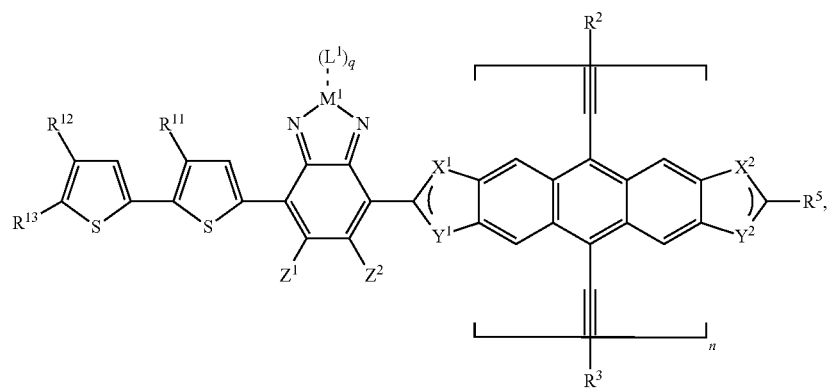

-continued

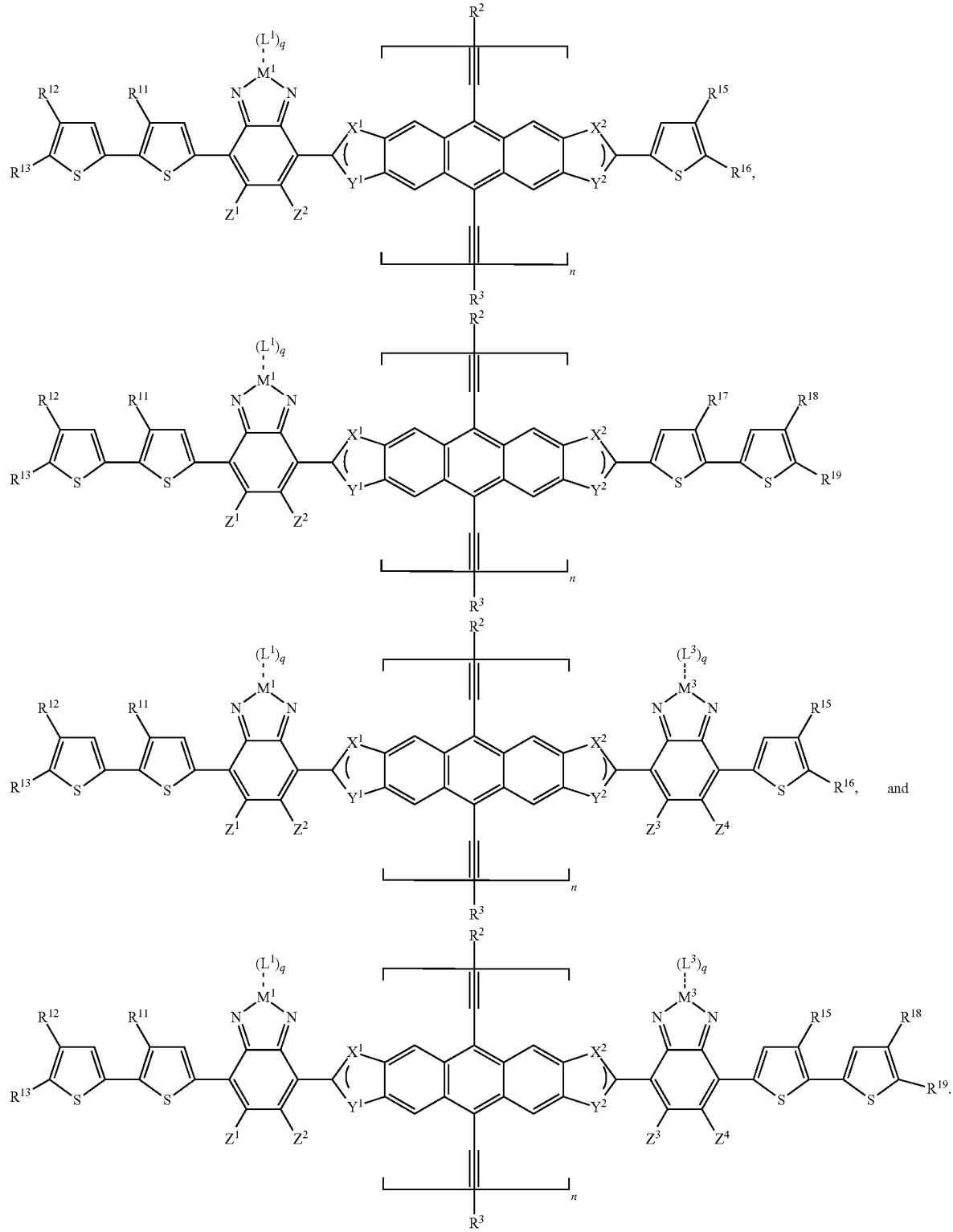

B. Organic Photovoltaic Cells

The small molecules and oligomers of the present invention can be used in photovoltaic applications, such as organic photovoltaic cells. FIG. 1 is a cross-sectional view of a non-limiting organic photovoltaic cell of the present invention, in which the photoactive layer is formed with the small molecules or oligomers of the present invention, or combinations thereof. Notably, polymers do not have to be used to form said photoactive layer. However, and if desired, polymers can be used in combination with the disclosed small molecules or oligomers. The organic photovoltaic cell (1) can include a transparent substrate (10), a front electrode (11), a photoactive layer (12), and a back electrode (13). Additional materials, layers, and coatings (not shown) known to those of ordinary skill in the art can be used with photovoltaic cell (1), some of which are described below.

Generally speaking, the organic photovoltaic cell (1) can convert light into usable energy by: (a) photon absorption to produce excitons; (b) exciton diffusion; (c) charge transfer; and (d) charge separation and transportation to the electrodes. With respect to (a), the excitons are produced by photon absorption by the photoactive layer (12), which can be a single layer such that the compounds of the present invention are the active light absorbing component in the layer. In preferred aspects, and given that the compounds of the present invention have both electron donor and acceptor regions, the preferred layer (12) is a bulk heterojunction single layer. However, multiple layers are also contemplated in the context of the present invention (e.g., a bi-layer, tri-layer, or multiple-layer staking or bulk heterojunction layers). For (b), the generated excitons diffuse to the p-n junction. Then in (c), the charge is transferred to the other constituent of the BHJ. For (d), electrons and holes are separated and transported to the electrodes (11) and (13) and are used in a circuit.

1. Substrate (10)

The substrate (10) can be used as support. For organic photovoltaic cells, it is typically transparent or translucent, which allows light to efficiently enter the cell. It is typically made from material that is not easily altered or degraded by heat or organic solvents, and as already noted, has excellent optical transparency. Non-limiting examples of such materials include inorganic materials such as alkali-free glass and quartz glass, polymers such as polyethylene, PET, PEN, polyimide, polyamide, polyamidoimide, polycarbonate (e.g., Lexan™, which is a polycarbonate resin offered by SABIC Innovative Plastics), liquid crystal polymer, and cycloolefin polymer, silicon, and metal.

2. Front Electrode and Back Electrodes (11) and (13)

The front electrode (11) can be used as a cathode or anode depending on the set-up of the circuit. It is stacked on the substrate (10). The front electrode (11) can be made of a transparent or translucent conductive material. Alternatively, the front electrode (11) can be made of opaque or reflective material. Typically, the front electrode (11) is obtained by forming a film using such a material (e.g., vacuum deposition, sputtering, ion-plating, plating, coating, etc.). Non-limiting examples of transparent or translucent conductive material include metal oxide films, metal films, and conductive polymers. Non-limiting examples of metal oxides that can be used to form a film include indium oxide, zinc oxide, tin oxide, and their complexes such as indium stannate (ITO), fluorine-doped tin oxide (FTO), and indium zinc oxide films. Non-limiting examples of metals that can be used to form a film include gold, platinum, silver, and copper. Non-limiting examples of conductive polymers include polyaniline and polythiophene. The thickness of the film for the front electrode (11) is typically between from 30 to 300 nm. If the film thickness is less than 30 nm, then the conductivity can be reduced and the resistance increased, which results in a decrease in photoelectric conversion efficiency. If the film thickness is greater than 300 nm, then light transmittance may be lowered. Also, the sheet resistance of the front electrode (11) is typically 10Ω/□ or less. Further, the front electrode (11) may be a single layer or laminated layers formed of materials each having a different work function.

The back electrode (13) can be used as a cathode or anode depending on the set-up of the circuit. This electrode (13) can be made of a transparent or translucent conductive material. Alternatively, it (13) can be made of opaque or reflective material. This electrode (13) can be stacked on the photoactive layer (12). The material used for the back electrode (13) can be conductive. Non-limiting examples of such materials include metals, metal oxides, and conductive polymers (e.g., polyaniline, polythiophene, etc.) such as those discussed above in the context of the front electrode (11). When the front electrode (11) is formed using a material having high work function, then the back electrode (13) can be made of material having a low work function. Non-limiting examples of materials having a low work function include Li, In, Al, Ca, Mg, Sm, Tb, Yb, Zr, Na, K, Rb, Cs, Ba, and the alloys thereof. The back electrode (13) can be a single layer or laminated layers formed of materials each having a different work function. Further, it may be an alloy of one or more of the materials having a low work function and at least one selected from the group consisting of gold, silver, platinum, copper, manganese, titanium, cobalt, nickel, tungsten, and tin. Examples of the alloy include a lithium-aluminum alloy, a lithium-magnesium alloy, a lithium-indium alloy, a magnesium-silver alloy, a magnesium-indium alloy, a magnesium-aluminum alloy, an indium-silver alloy, and a calcium-aluminum alloy. The film thickness of the back electrode (13) can be from 1 to 1000 nm or from 10 to 500 nm. If the film thickness is too small, then the resistance can be excessively large and the generated charge may not be sufficiently transmitted to the external circuit.

In some embodiments, the front (11) and back (13) electrodes can be further coated with hole transport or electron transport layers (not shown in FIG. 1) to increase the efficiency and prevent short circuits of the organic photovoltaic cell (1). The hole transport layer and the electron transport layer can be interposed between the electrode and the photoactive layer (12). Non-limiting examples of the materials that can be used for the hole transport layer include polythiophene-based polymers such as PEDOT/PSS (poly(3,4-ethylenedioxythiophene)-poly(styrene sulfonate)) and organic conductive polymers such as polyaniline and polypyrrole. The film thickness of the hole transport layer can be from 20 to 100 nm. If the film thickness is too low, short circuit of the electrode can occur more readily. If the film thickness is too high, the film resistance is large and the generated electric current could be limited and optical conversion efficiency can be reduced. As for the electron transport layer, it can function by blocking holes and transporting electrons more efficiently. Non-limiting examples of the type of material that the electron transport layer can be made of include metal oxides (e.g., amorphous titanium oxide). When titanium oxide is used, the film thickness can range from 5 to 20 nm. If the film thickness is too low, the hole blocking effect can be reduced and thus the generated excitons are deactivated before the excitons dissociate into electrons and holes. By comparison, when the film thickness is too high, the film resistance is large, the generated electric current is limited, resulting in reduction of optical conversion efficiency.

3. Photoactive Layer (12)

The photoactive layer (12) can be an organic or hybrid semiconducting or conducting layer. The layer (12) can be interposed between the front electrode (10) and the back electrode (13). In one preferred instance, the photoactive layer (12) can be a bulk hetero junction single layer such that the compounds of the present invention are the active light absorbing component in the layer. The layer (12) can absorb light and allow for the flow of electrons to and from the electrodes (11 and 13). Further, there can be multiple photoactive layers used for a given photovoltaic cell (e.g., 2, 3, 4, or more).

Given the unique properties of the compounds (i.e., small molecules and oligomers) of the present invention, many options are available for forming the photoactive photoactive layer (12) on at least a portion of a surface of the electrodes (11 and 13) or on the substrate (10) or both. By way of example, vacuum thermal evaporation, which involves the heating of an organic material in vacuum and depositing said material, or organic vapor phase deposition, which involves evaporation of the organic material over a substrate in the presence of an inert carrier gas, can be used. However, the increased solubility of the compounds of the present invention also allows for the formation of a solution that can then be deposited onto said surfaces. In particular, the compounds of the present invention can be fully or partially solubilized within a solution and then deposited onto a given surface via solution-based deposition techniques (e.g., spray coating, role-to-role coating, drop casting, dip coating, Mayer rod coating, doctor blade coating, spin coating, meniscus coating, transfer printing, ink jet printing, offset printing, screen printing, gravure printing, flexo printing, dispenser coating, nozzle coating, capillary coating, etc.). Non-limiting examples of solvents that can be used in the context of the present invention include unsaturated hydrocarbon-based solvents (such as toluene, xylene, tetralin, decalin, mesitylene, n-butylbenzene, sec-butylbutylbenzene, and tert-butylbenzene), halogenated aromatic hydrocarbon-based solvents (such as chlorobenzene, dichlorobenzene, and trichlorobenzene), halogenated saturated hydrocarbon-based solvents (such as carbon tetrachloride, chloroform, dichloromethane, dichloroethane, chlorobutane, bromobutane, chloropentane, chlorohexane, bromohexane, and chlorocyclohexane), ethers (such as tetrahydrofuran and tetrahydropyran), and polar aprotic solvents (such as dichloromethane (DCM), tetrahydrofuran (THF), ethyl acetate, propyl acetate, butyl acetate, isobutylacetate (and the like), acetone, dimethylformamide (DMF), acetonitrile (MeCN), benzonitrile, nitromethane, dimethyl sulfoxide (DMSO), propylene carbonate, or N-methyl-2-pyrrolidone (NMP), sulfolane (tetramethylene sulfone, 2,3,4,5-tetrahydrothiophene-1,1-dioxide), hexamethylphosphoramide (HMPA), methyl ethyl ketone, methyl isobutyl ketone, acetophenone, benzophenone, or the like), or any combination of said solvents.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Synthesis of 2,8-Bis(5-fluoro-7-(5'-hexyl-[2,2'-bithiophene]-5-yl)benzo[c]-[1,2,5]thiadiazole)-5,11-Bis(triisopropylsilylethynyl)anthra[2,3-b:6,7-b']dithiophene and 2,8-Bis(5-fluoro-7-(5'-hexyl-[2,2'-bithiophene]-5-yl)benzo[c][1,2,5]thiadiazole)-5,11-bis-(triisopropylsilylethynyl)anthra[2,3-b:7,6-b']dithiophene Synthesis of 5-Bromo-2,3-thiophenedicarboxaldehyde (1)

Bromine (6.0 mL, 116.3 mmol) was added drop wise at room temperature to a solution of 2,3-thiophenedicarboxaldehyde (5.1 g, 36.38 mmol) in 100 mL of $CHCl_3$. The reaction mixture was stirred overnight and then excess bromine was quenched with a saturated solution of $Na_2S_2O_3$. The organic layer was extracted with $CHCl_3$, dried over $Na_2SO_4$ and volatiles were removed in vacuo to obtain 1 as a brown solid. Spectroscopically pure compound was isolated by column chromatography using silica gel as stationary phase and a 4:1 mixture of $CH_2Cl_2$:hexanes. $^1H$ NMR (500 MHz, $CDCl_3$): δ1 0.37 (s, 1H), 10.26 (s, 1H), 7.59 (s, 1H).

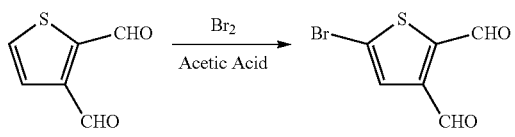

Alternate procedure for the synthesis of 5-Bromo-2,3-thiophenedicarboxaldehyde (1 and 2)

Bromine (1.2 mL, 7.5 mmol) was added drop wise to a solution of 2,3-thiophenedicarboxaldehyde (1.0 g, 7.1 mmol) in 20 mL of glacial acetic acid. The reaction mixture was stirred overnight at 70° C. and then excess bromine was quenched with a saturated solution of $Na_2S_2O_3$. The organic layer was extracted with $CH_2Cl_2$, dried over $Na_2SO_4$ and volatiles were removed in vacuo to obtain a mixture of 1 and 4,5-dibromo-2,3-thiophenedicarboxaldehyde 2 as a brown solid (30:65 by $^1H$ NMR spectroscopy). Spectroscopically pure compound was isolated by column chromatography using silica gel as stationary phase and a 4:1 mixture of $CH_2Cl_2$:hexanes. $^1H$ NMR (500 MHz, $CDCl_3$): δ 10.37 (s, 1H), 10.26 (s, 1H), 7.59 (s, 1H). $^1H$ NMR data for 4,5-dibromo-2,3-thiophenedicarboxaldehyde (500 MHz, $CDCl_3$): δ 9.81 (s, 1H), 7.36 (s, 1H).

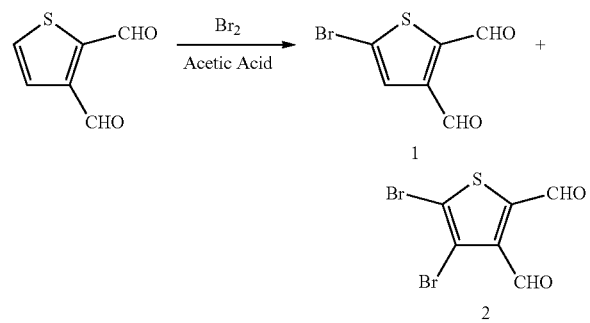

Synthesis of 2,8-dibromoanthradithiophenequinones (3)

To a mixture of 1 (2.0 g, 9.18 mmol) and 1,4-cyclohexanedione (50 mg, 0.46 mmol) 10 mL of ethanol was added and afterwards an ethanol solution of KOH (15%, 0.5 mL) was added to the reaction mixture. The resulting brown slurry was stirred at room temperature for 3 hours and then filtered and washed with ethanol to obtain 3 as a pale brown powder.

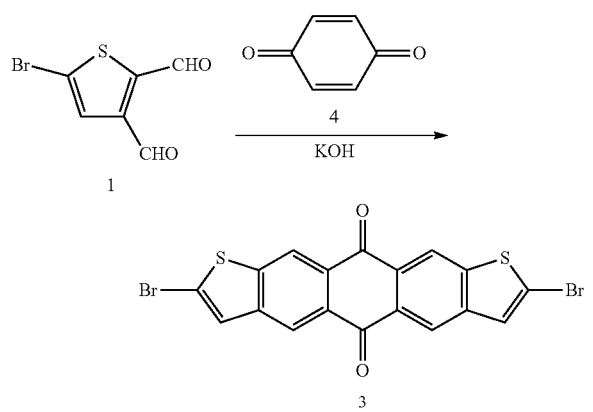

Synthesis of Anthra[2,3-b:6,7-b']dithiophene-5,11-dione and Anthra[2,3-b:7,6-b']dithiophene-5,11-dione (4)

To a solution of thiophene-2,3-dicarboxaldehyde (2.0 g, 17.2 mmol) in 200 mL of EtOH was stirred at room temperature followed by addition of 1,4-cyclohexane dione (0.96 g, 8.6 mmol). Afterwards, a solution of 15% KOH was added to the reaction mixture to form brown precipitate. The resulting reaction mixture was stirred for an additional 3 h and then filtered to obtain a pale yellow powder in quantitative yield. Compounds 4 and 6 could not be characterized due to their poor solubility in common organic solvents. HR-mass spectroscopy confirmed formation of the products.

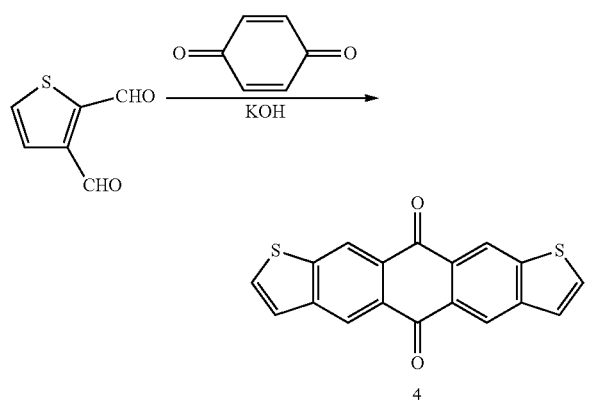

Synthesis of 5,11-Bis(triisopropylsilylethynyl)anthrax[2,3-b:6,7-b']dithiophene and 5,11-Bis(triisopropylsilylethynyl)anthrax[2,3-b:7,6-b']dithiophene (5)

nBuLi (7.8 mL, 1.6 M solution in hexanes) was added drop wise to triisopropysilylacetylene (2.95 mL, 13.2 mmol) and then heated at 60° C. for 1 hour. After cooling the reaction mixture to room temperature, compound 4 was added under nitrogen stream and heated overnight at 60° C. to obtain a dark brown solution. Afterwards, a solution of stannyl chloride dehydrate (3.0 g, 13.8 mmol) in 10% HCl solution was added and heated again to 60° C. for 2 hours to yield a dark pink solution. The crude product was obtained after filtering through a silica gel flash column using hexanes as eluent. Spectroscopically pure 5 was isolated as dark red crystals after recrystallization from hexanes at 35° C. in 38% yield.

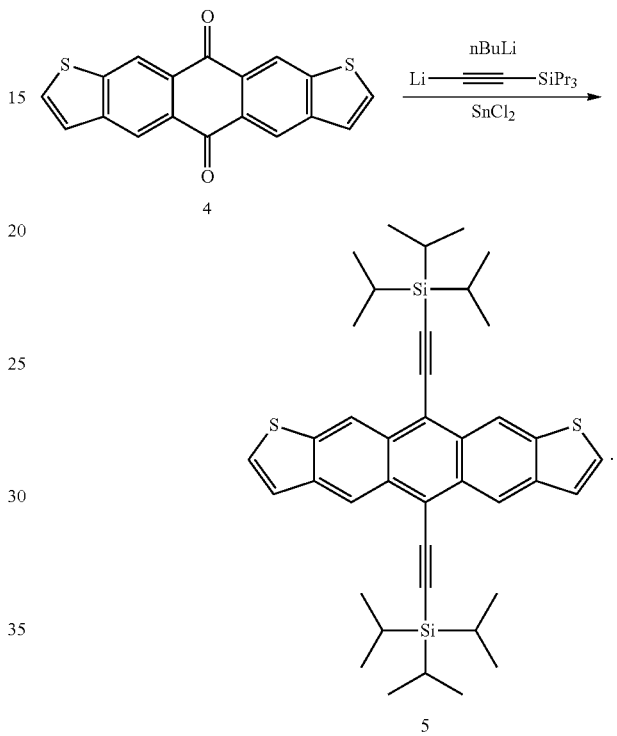

Synthesis of 2,8-Bis(trimethylstannyl)-5,11-Bis(triisopropylsilylethynyl)-anthra[2,3-b:6,7-b']dithiophene and 2,8-Bis(trimethylstannyl)-5,11-Bis(triisopropylsilyl-ethynyl)anthra[2,3-b:7,6-b']dithiophene (6)

To a cold (−78° C.) solution of compound 5, (1.0 g, 1.54 mmol) in 15 mL of dry THF was added LDA (1.6 mL, 2 M solution in THF) and stirred at that temperature for 1 hour. Afterwards, trimethyltin chloride (3.4 mL, 1 M solution in THF) was added to the reaction mixture drop wise at −78° C., then warmed gradually to room temperature and stirred overnight. After quenching the reaction with water organic layer was extracted with hexanes, dried over $Na_2SO_4$ and volatiles were removed to obtain 95% pure 6 as red powder. Crystals suitable for X-ray crystallography were obtained by recrystallization from hexanes at −35° C. $^1$H NMR (500 MHz, $CDCl_3$): δ 9.19 (m, 2H), 9.10 (m, 2H), 7.50 (s, 2H, 3JSnH=29.5 Hz), 1.32 (m, 42H), 0.49 (s, 18H). 13C (1H) (500 MHz, $CDCl_3$): δ −8.4 ($Sn(CH_3)_3$), 11.7 ($CH(CH_3)_3$), 19.1 ($CH(CH_3)_3$), 104.5 (CC—Si), 105.5 (—CC), 116.4 (ArC), 117.7 (ArC), 118.9 (ArC), 120.1 (ArC), 129.6 (ArC), 129.8 (ArC), 129.9 (ArC), 130.2, (ArC), 131.7 (ArC), 141.2 (ArC), 141.3 (ArC), 143.1 (ArC), 143.2 (ArC), 145.9 (ArC), 146.1 (ArC). 119Sn NMR (185 MHZ, $CDCl_3$): δ −23.7. LR MALDI, Calculated for $C_{46}H_{66}S_2Si_2Sn_2$: 976[M+]. Anal. calculated for $C_{46}H_{66}S_2Si_2Sn_2$: C, 56.57; H, 6.81; S, 6.57. Found: C, 56.89; H, 6.93; S, 6.18.

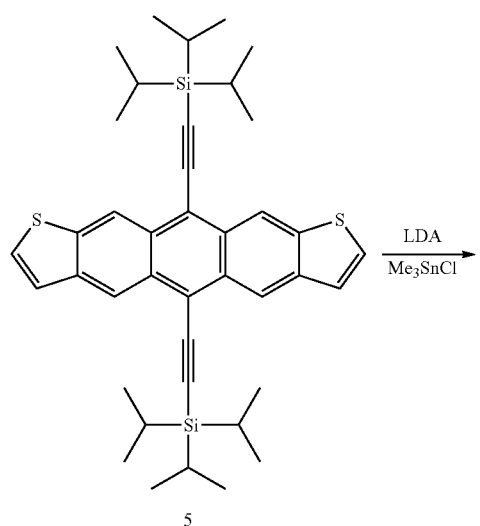

5

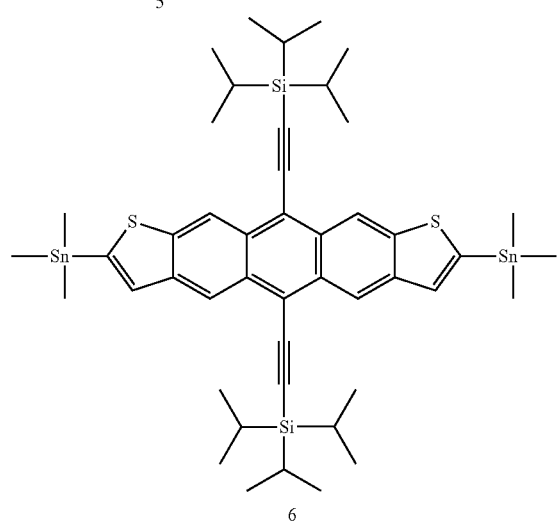

6

Figure 2A:
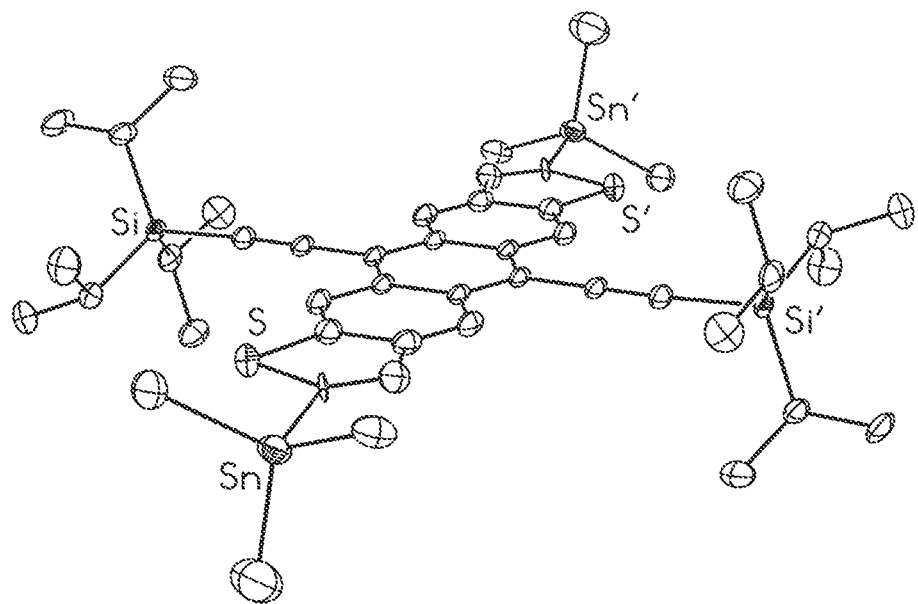
FIGS. 2A-B: Thermal ellipsoid plots of compound 6.
Figure 2B:
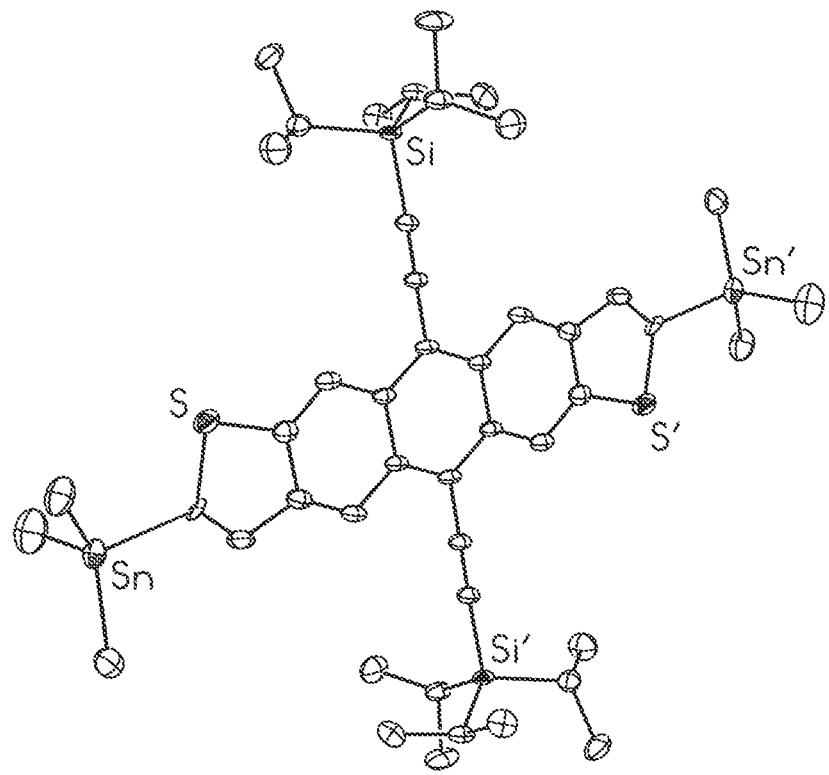

FIGS. 2A and B provide two different view of thermal ellipsoid plots of compound 6.

Synthesis of 2,8-Bis(5-fluoro-7-(5'-hexyl-[2,2'-bithiophene]-5-yl)benzo[c]-[1,2,5]thiadiazole)-5,11-bis(triisopropylsilylethynyl)anthra[2,3-b:6,7-b']dithiophene and 2,8-Bis(5-fluoro-7-(5'-hexyl-[2,2'-bithiophene]-5-yl)benzo[c][1,2,5]thiadiazole)-5,11-bis-(triisopropylsilylethynyl)anthra[2,3-b:7,6-b'] dithiophene (8)

A 20 mL microwave glass tube was charged with 7 (196 mg, 0.41 mmol), 6 (200 mg, 0.2 mmol), Pd(PPh$_3$)$_4$ (15 mg, 0.013 mmol) and 15 mL dry THF. The glass tube was sealed with a Teflon® cap and stirred at room temperature for 15 minutes. Afterwards, the reaction mixture was heated to 100° C. for 2 minutes, 125° C. for 2 minutes, 140° C. for 10 minutes, 150° C. for 12 minutes and 160° C. for 15 minutes in a Biotage microwave reactor. After cooling the reaction mixture to room temperature, the crude product mixture was then added to a aqueous solution of sodium diethyldithiocarbamate (1 g/100 mL) and stirred for 12 hours at room temperature. Afterwards, the organic layer was separated and volatiles were removed to obtain crude product as a dark brown powder. Compound 8 was purified by washing with toluene, dichloromethane and methanol (278 mg, 70%). NMR studies are incomplete due to insolubility of 7 in common organic solvents (only dissolves in dichlorobenzene at 170° C.). LR MALDI, calculated for $C_{80}H_{84}F_2N_4S_8Si_2$: 1,450 [M+]. Anal. calculated for $C_{80}H_{84}F_2N_4S_8Si_2$: C, 66.16; H, 5.83; N, 3.86; S, 17.66. Found: C, 63.29; H, 5.56; N, 3.61; S, 18.01. Compound 8 is highly crystalline and forms wire like structure during the reaction probably due to the presence of strong intermolecular π-π stacking.

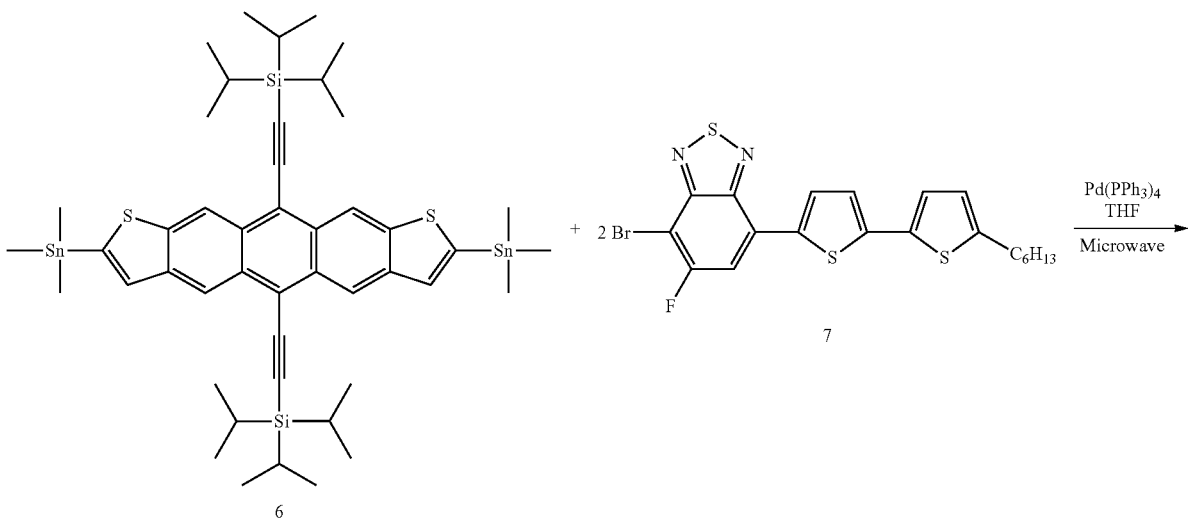

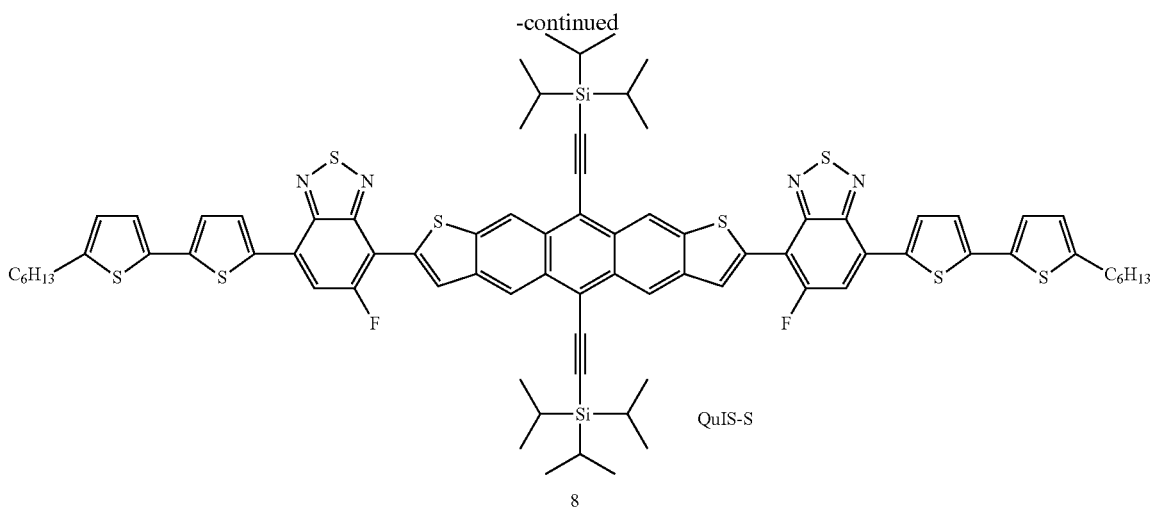

QuIS-S
8

Example 2

Synthesis of 2,8-Bis(5-fluoro-7-(5'-hexyl-[2,2'-bithiophene]-5-yl)benzo[c]-[1,2,5]seleno-diazole)-5,11-bis(triisopropylsilylethynyl)anthra[2,3-b:6,7-b']dithiophene and 2,8-Bis(5-fluoro-7-(5'-hexyl-[2,2'-bithiophene]-5-yl)benzo[c][1,2,5]seleno-diazole)-5,11-bis-(triisopropylsilylethynyl)anthra[2,3-b:7,6-b']dithiophene (10)

Synthesis of 10

A 20 mL microwave vial was charged with 9 (216 mg, 0.41 mmol), 6 (200 mg, 0.2 mmol), Pd(PPh$_3$)$_4$ (15 mg, 0.013 mmol) and 15 mL of dry THF. The glass tube was sealed with a Teflon® cap and stirred at room temperature for 15 minutes. Afterwards, the reaction mixture was heated to 100° C. for 2 minutes, 125° C. for 2 minutes, 140° C. for 10 minutes, 150° C. for 10 minutes, 160° C. for 20 minutes and 170° C. for 30 minutes in a Biotage microwave reactor. After cooling the reaction mixture to room temperature, the crude product mixture was then added to a aqueous solution of sodium diethyldithiocarbamate (1 g/100 mL) and stirred for 12 hours at room temperature. Afterwards, the organic layer was separated and volatiles were removed to obtain crude product as a dark brown powder. The crude material was washed with a mixture of CH$_2$Cl$_2$/hexanes (5:1, 4×30 mL) to obtain pure 10 as a dark brown powder (210 mg, 54%). NMR studies are incomplete due to insolubility of 9 in common organic solvents. LR MALDI, calculated for C$_{80}$H$_{84}$F$_2$N$_4$S$_6$Se$_2$Si$_2$: 1546.1 [M+1]. Anal. calculated for C$_{80}$H$_{84}$F$_2$N$_4$S$_6$Se$_2$Si$_2$: C, 62.15; H, 5.48; N, 3.62; S, 12.44. Found: C, 62.04; H, 5.44; N, 3.62; S, 12.41. HRMS (MALDI-TOF), Calculated for C$_{80}$H$_{84}$F$_2$N$_4$S$_6$Se$_2$Si$_2$: 1546.2870 [M+]. found 1546.2850.

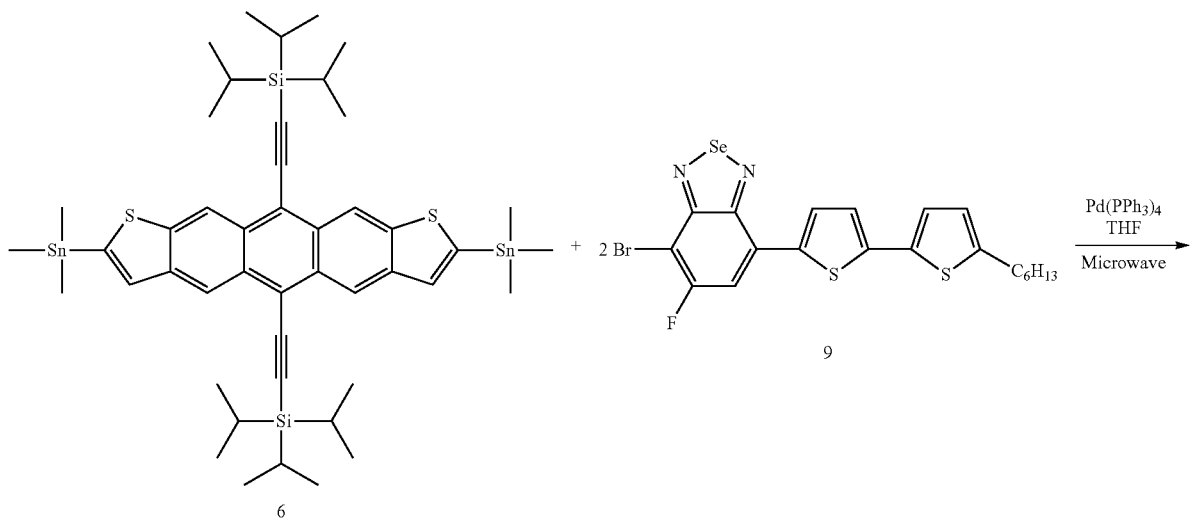

-continued

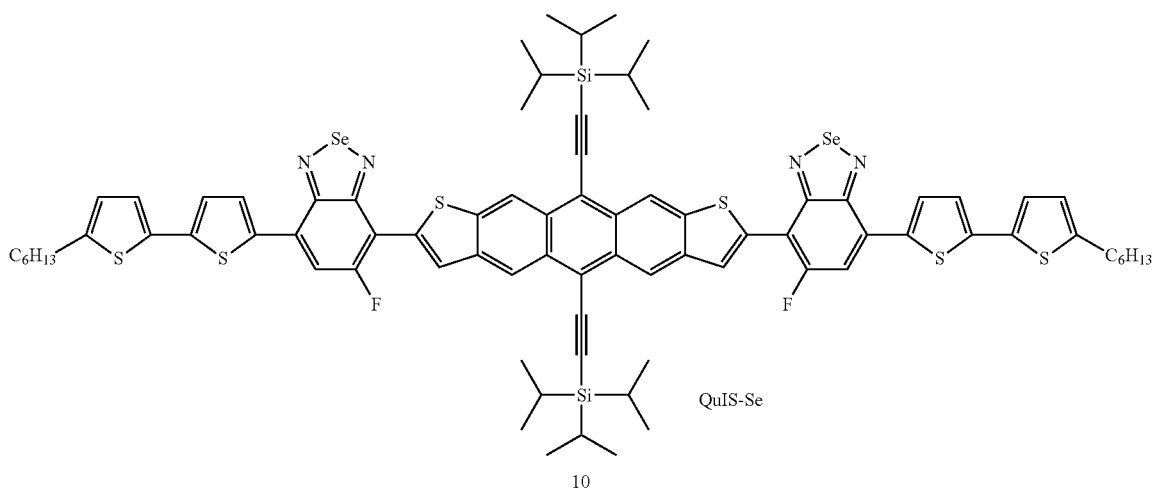

QuIS-Se

10

Example 3

Data Concerning Compounds 8 and 10

Figure 3A:
FIGS. 3A-C: Scanning electron microscopy (SEM) images of QuIS-S crystals suspended on standard transmission electron microscopy (TEM) grids.
Figure 3B:
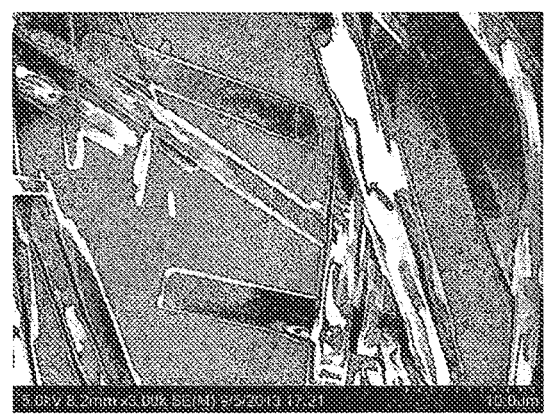
Figure 3C:
Figure 4:
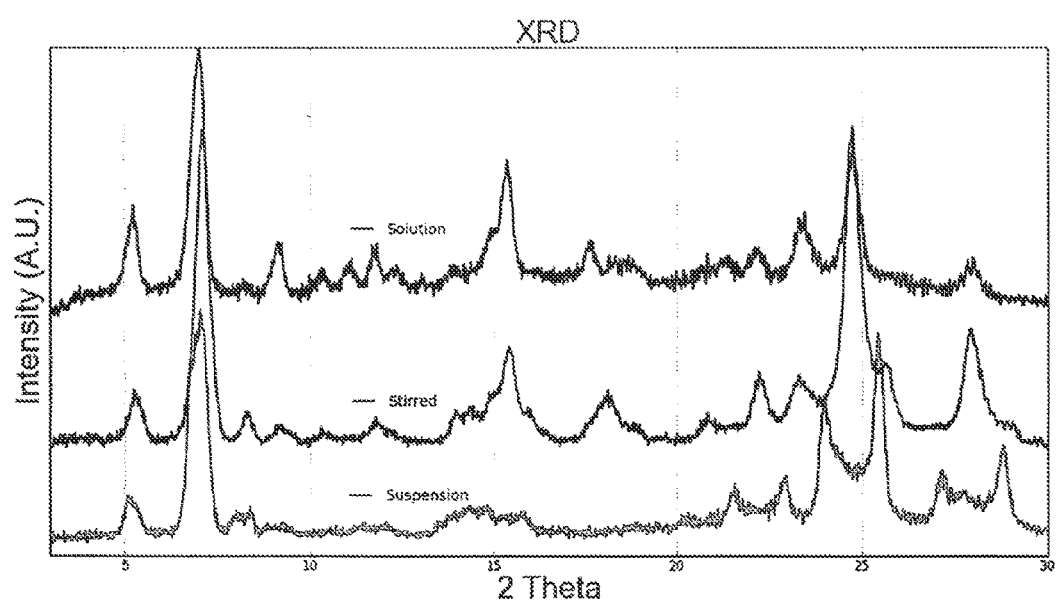
FIG. 4: XRD of QuIS-S prepared under different conditions.

Crystal Structure:

Compound 8 has a crystalline structure as suggested by the uniform and linear structures viewed by scanning electron microscope (SEM) and X-ray diffraction (XRD) patterns, illustrated in FIGS. 3 and 4, respectively.

Solubility:

Compounds 8 and 10 were screened with a variety of polar and non-polar solvents to try to dissolve the compounds. No dissolution occurred. It was discovered that heating the compounds in dichlorobenzene to 160 to 165° C., without stirring, induced the formation of a dark transparent solution that could be used to produce coherent films with the compounds. The FIG. 4 XRD spectra refer to three situations: (i) "Solution" refers to getting the compounds to solubilize prior to casting a film (165° C., no stirring); (ii) "Stirred" refers to stirring the solution without heating and prior to casting of a film; and (iii) "Suspension" refers to the addition of a solvent without any noticeable dissolution of the compound. A difference in the higher 2 theta values in FIG. 4, near 25°, is suggestive of a hypothesized switch between a molecule with a $C_2$-symmetric rotation axis, and one without a rotational axis. The compounds 8 and 10 have the $C_2$-rotation axis.

Figure 5:
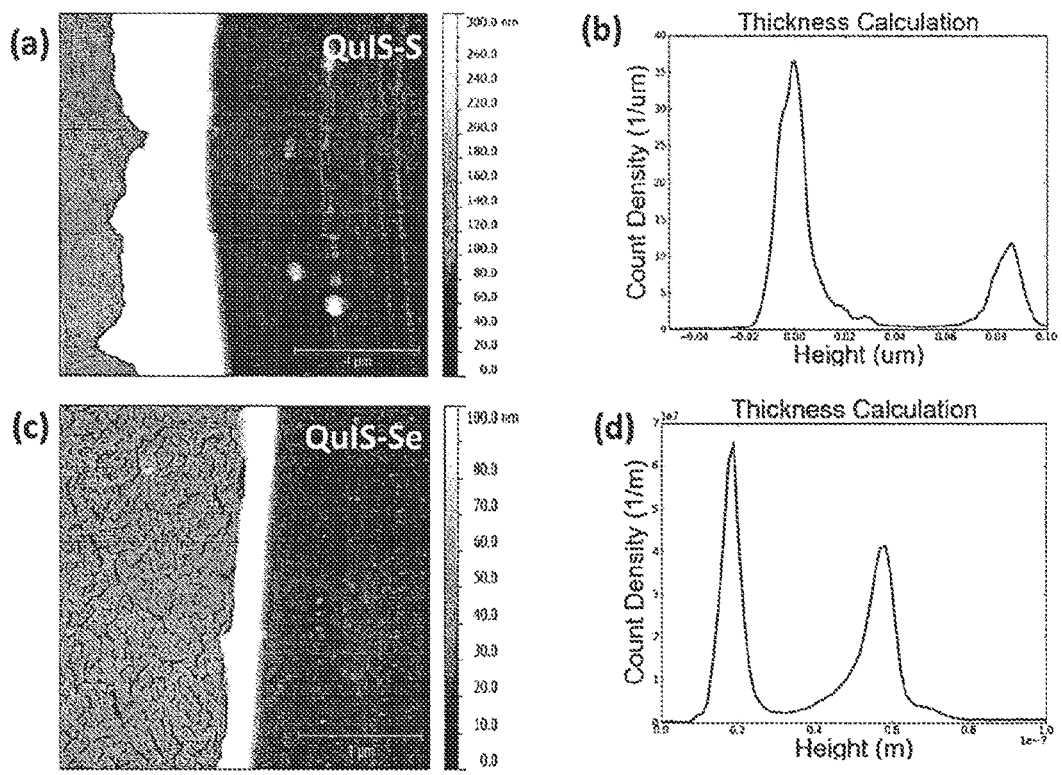
FIGS. 5A-D: Atomic Force Microscopy (AFM) images showing the determination of thickness of films of QuIS-S and QuIS-Se on glass.
Figure 6:
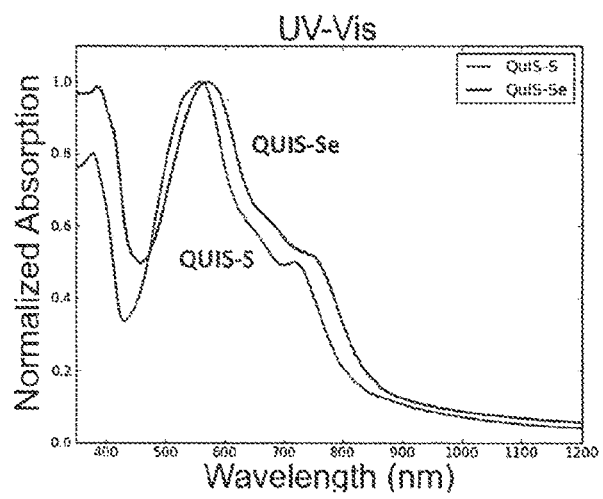
FIG. 6: UV-Vis spectra of both QuIS-S and QuIS-Se films.
Figure 7:
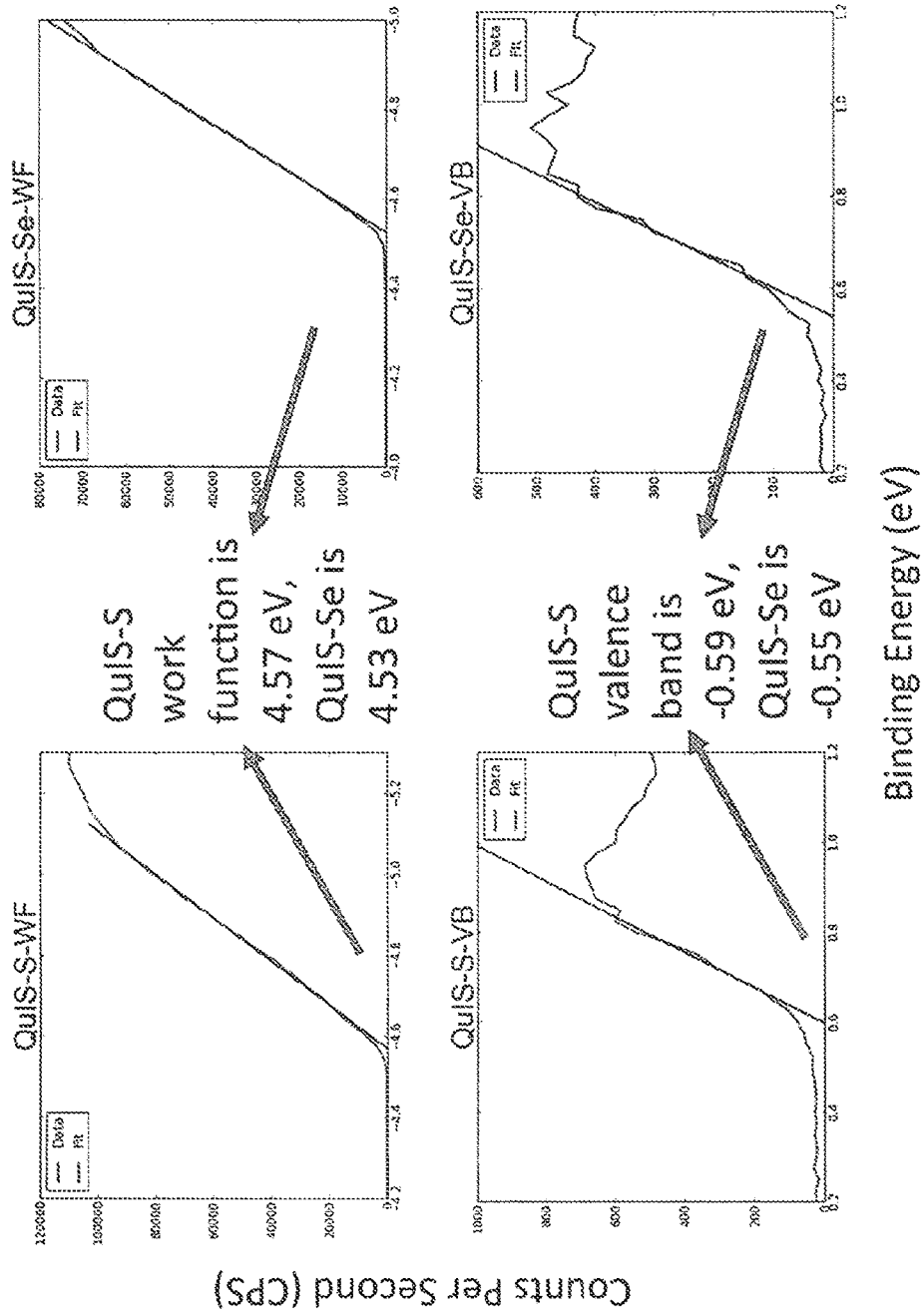
FIG. 7: Tauc plots for QuIS-S and QuIS-Se films.
Figure 8:
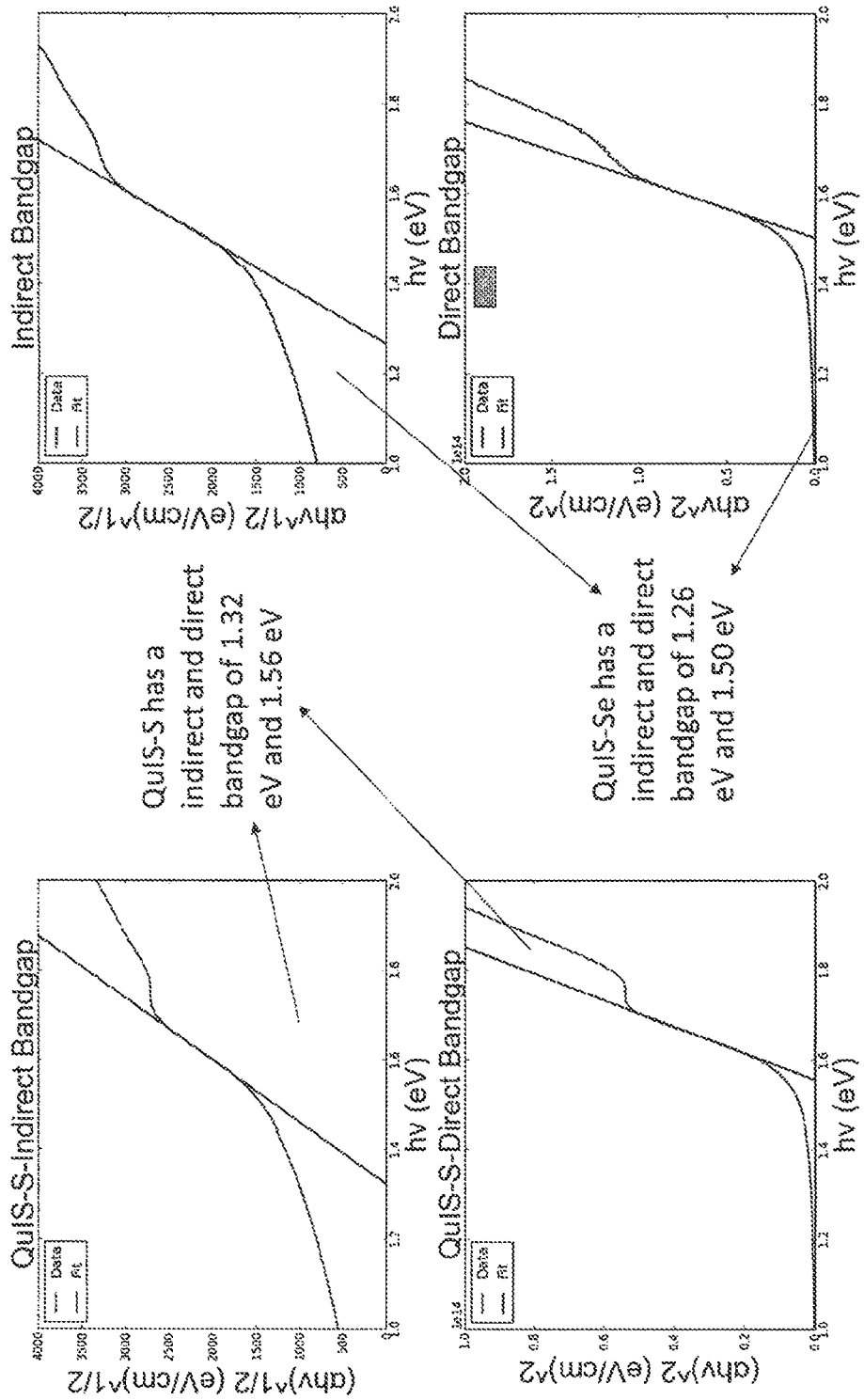
FIG. 8: Ultraviolet photoelectron spectroscopy (UPS) for QuIS-S and QuIS-Se films.
Figure 9:
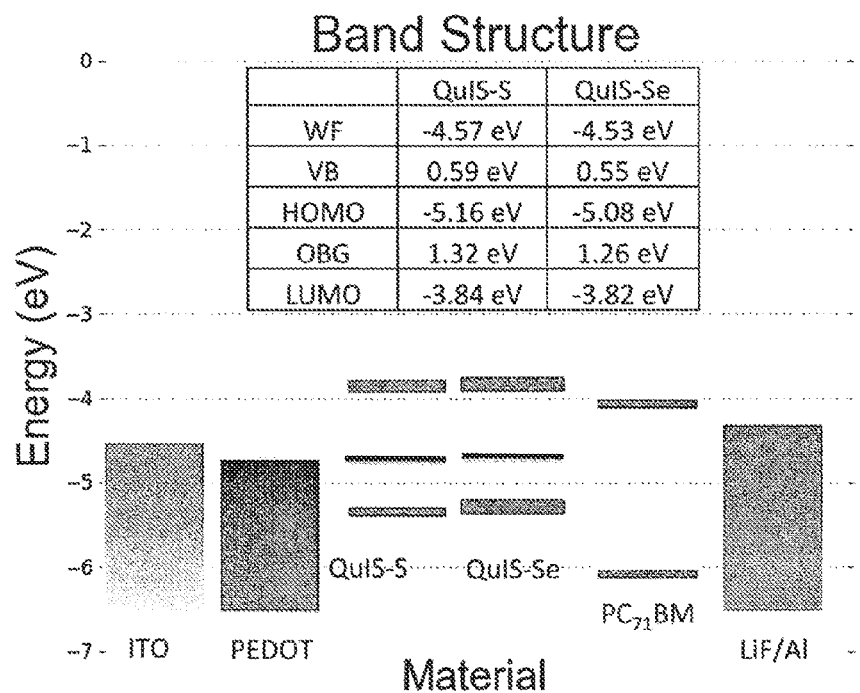
FIG. 9: Proposed band diagram for both QuIS-S and QuIS-Se.

Film Formation on Glass Substrate:

FIG. 5 illustrates atomic force microscopy (AFM) images of films formed from compounds 8 (QuIS-S) and 10 (QuIS-Se) on a glass substrate. The films were cast from a solution of 5 mg/ml of compounds 8 and 10, respectively, in dichlorobenzene at 165° C. FIG. 6 provides UV-Vis spectra of the compound QuIS-S and QuIS-Se films. The glass background has been subtracted and the absorbance normalized in FIG. 6. Once smooth and relatively defect-free films were prepared via the higher temperature odichlorobenzene processing to yield a solution, the thickness can be controlled, and thus electronic properties can be measured with accuracy. Tauc plots in FIG. 7 of the QuIS-S and QuIS-Se films illustrate the presence of direct and indirect band gaps. For QuIS-S, the gaps are 1.32 eV for the indirect, and 1.56 eV for the direct gap, whereas with QuIS-Se, the gaps are 1.26 eV for the indirect, and 1.50 eV for the direct gap. FIG. 8 provides ultraviolet photoelectron spectroscopy (UPS) for both films. The top two plots show the measurements from a work function scan, while the bottom two plots show the values of the valence band scan. FIG. 9 provides a proposed band diagram for both films, based upon the data from the Tauc plots and known values for ITO, PEDOT:PSS, PC71BM, and LiF/Al.

Figure 10:
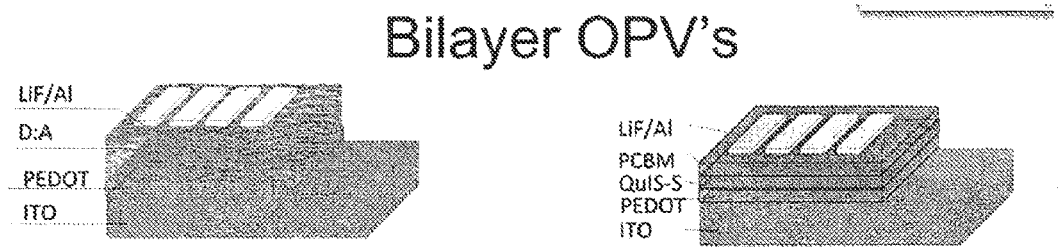
FIG. 10: Illustration of a bilayer OPV using a QuIS-S film and a PC71BM film.

Bi-Layer Electronic Device:

FIG. 10 illustrates a produced bilayer OPV with a QuIS-S film and a PC71BM film. Table 1 provides data concerning the produced OPV:

TABLE 1

| Condition | Jsc | Voc | PCE | FF | Series | Shunt |
|---|---|---|---|---|---|---|
| Solvent Anneal (120° C. + DCB) | −2.9 (0.2) | 0.45 (0.04) | 0.56 (0.1) | 0.42 (0.06) | 7.7 (0.6) | 0.09 (0.03) |
| As Spin Cast | −3.2 (0.1) | 0.49 (0.03) | 0.74 (0.1) | 0.46 (0.04) | 7.6 (0.6) | 0.18 (0.08) |
| Thermal Anneal (120° C.) | −2.9 (0.2) | 0.33 (0.05) | 0.36 (0.08) | 0.37 (0.04) | 7.3 (0.7) | 0.014 (0.006) |
| Best | −3.7 (0.4) | 0.61 (0.01) | 1.12 (0.08) | 0.51 (0.03) | 16.7 (5) | 0.6 (0.1) |

Figure 11:
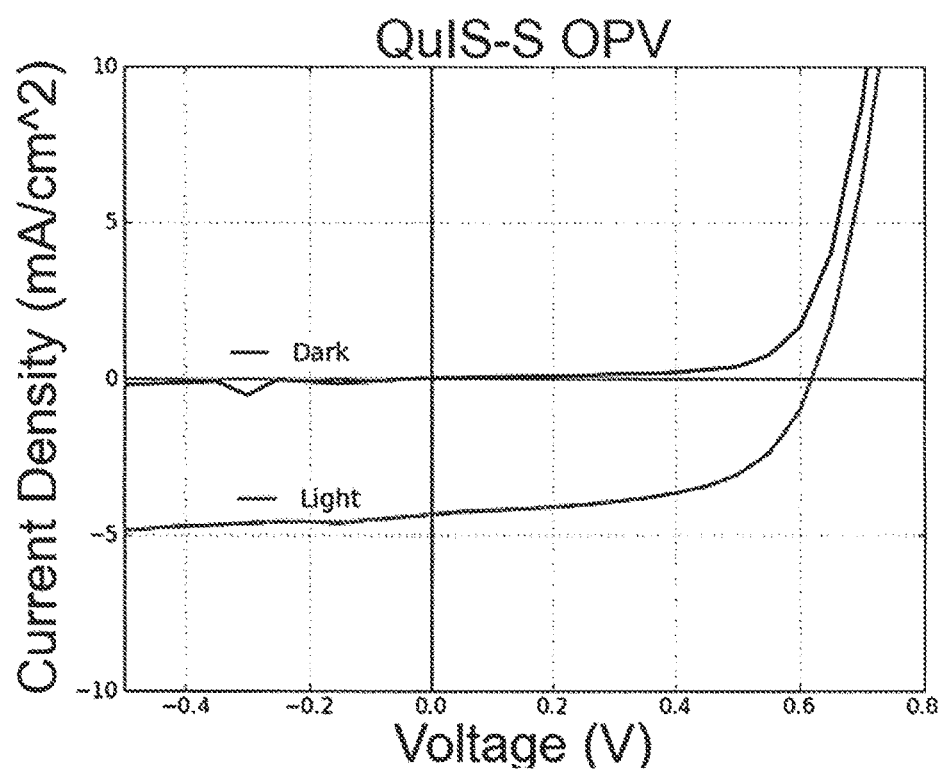
FIG. 11: I-V curve using QuIS-S in a bilayer configuration with PC71BM.

FIG. 11 provides I-V curve illustrating the best results obtained using the QuIS-S film in a bilayer configuration with a PC71BM film.

Figure 12:
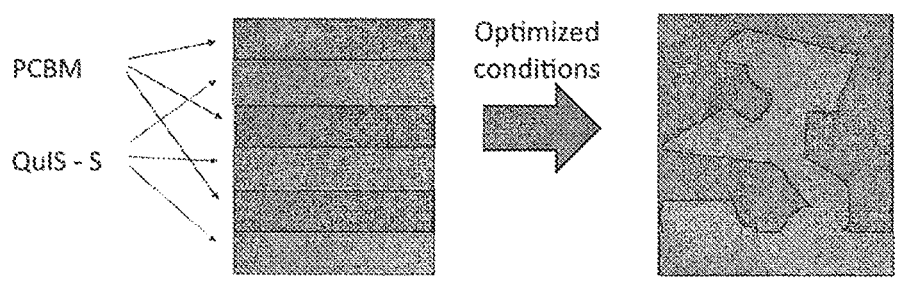
FIG. 12: Illustration of PC71 BM and QuIS-S films intermingling to form an in-situ BHJ.

Proposed Bulkheterojunction (BHJ) Electronic Device:

FIG. 12 provides an illustration of a PC7lBM and QuIS-S bulkheterojunction (BHJ) electronic device that could be prepared in the context of the present invention.

The invention claimed is:
1. A compound having the following structure:

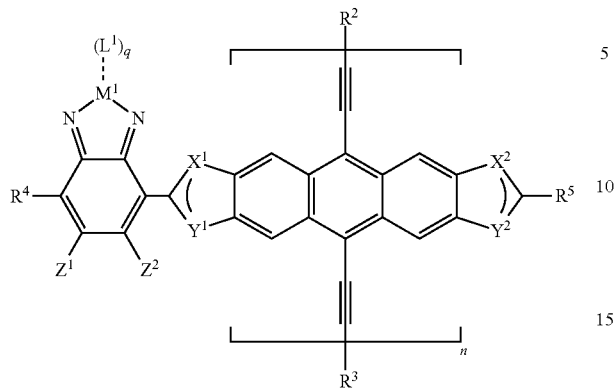

wherein:
one of $X^1$ and $Y^1$ is —CH= or =CH— and the other is S, O, CH$_2$ or NR$^1$;
one of $X^2$ and $Y^2$ is —CH= or =CH— and the other is S, O, CH$_2$ or NR$^1$;
$R^1$ is H or a linear or branched aliphatic group of up to 20 carbon atoms;
$R^2$ and $R^3$ are each independently

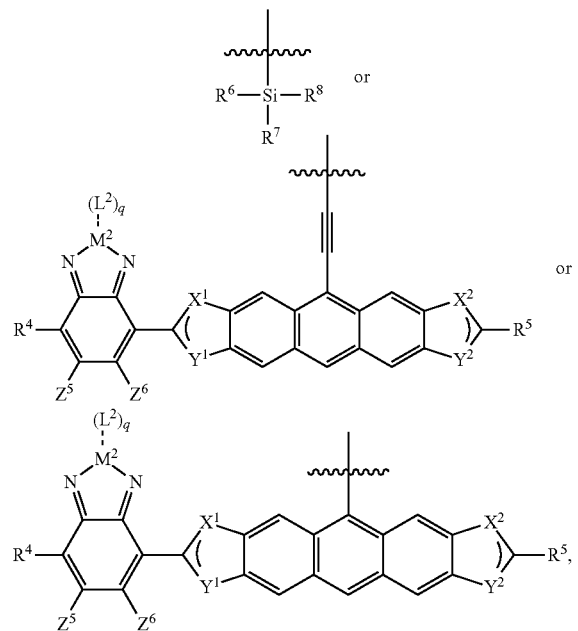

where
$R^4$ is

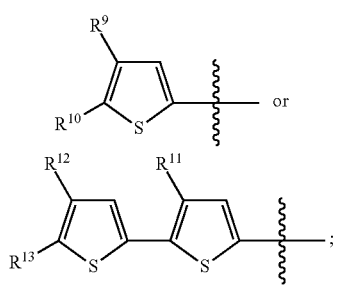

$R^5$ is

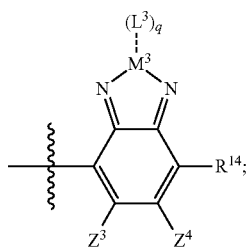

$R^{14}$ is

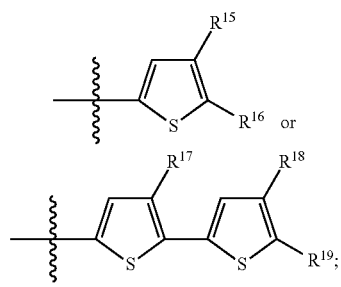

and
$R^9, R^{10}, R^{11}, R^{12}, R^{13}, R^{15}, R^{16}, R^{17}, R^{18}$ and $R^{19}$ are each independently H, or a linear, branched or cyclic aliphatic, aryl or heteroaryl group of up to 20 carbon atoms, with the proviso that both of $R^6$ and $R^7$ are not H, both of $R^9$ and $R^{10}$ are not H, both of $R^{12}$ and $R^{13}$ are not H, and both of $R^{15}$ and $R^{16}$ are not H;
$M^1$, $M^2$, and $M^3$ are each individually S, Se, or Te;
$L_1$, $L_2$, and $L_3$ are each individually a coordination ligand bound to $M^1$, $M^2$, and $M^3$, respectively, through a coordination bond, with q being an integer from 0 to 4;
$Z_1, Z_2, Z_3, Z_4, Z_5$ and $Z_6$ are each independently H, Cl, Br, F, NO$_2$, CN, N(R$_{20}$)$_2$, OR$_{21}$, CF$_3$, or C$_6$H$_z$E$_{6-z}$, or $Z_1$ and $Z_2$ or $Z_3$ and $Z_4$ or $Z_5$ and $Z_6$ are each N and are connected by a metal bridge atom to form, together with the carbon atoms to which they are attached, a 5 member ring system, where
$R_{20}$ and $R_{21}$ are each independently a linear, branched or cyclic aliphatic, aryl or heteroaryl group of up to 20 carbon atoms,
X is F, Cl or Br, and
z is an integer from 0 to 6; and
n is an integer from 0 to 5.
2. The compound of claim 1, having the following structure:

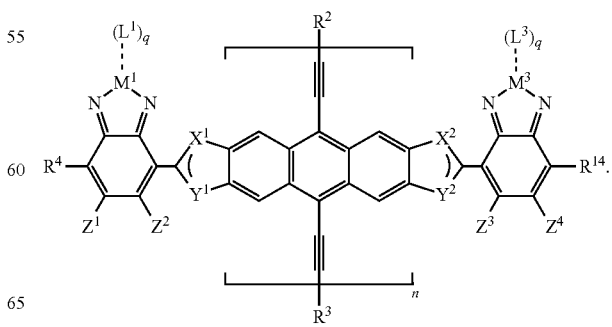

3. The compound of claim 1, having the following structure:

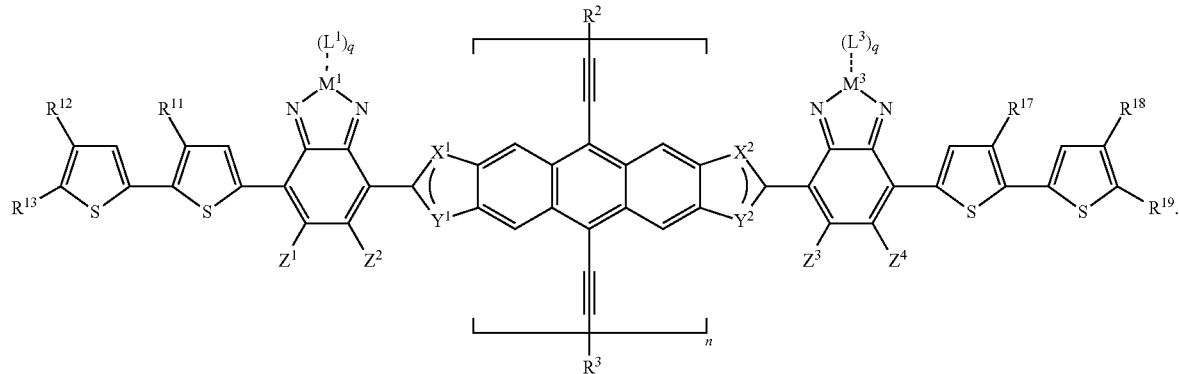

4. The compound of claim 1, having the following structure:

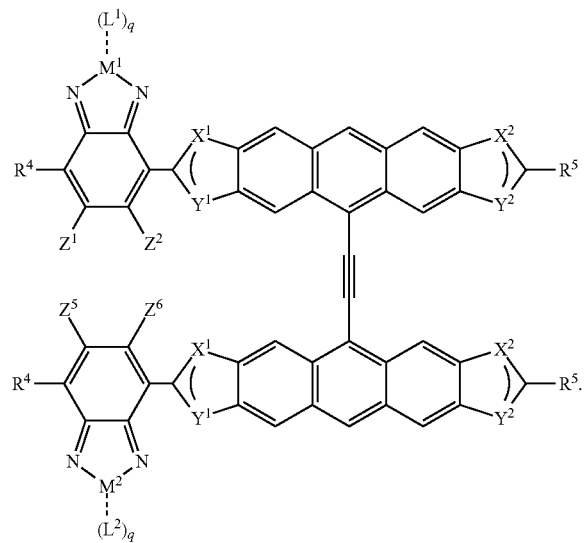

5. The compound of claim 1, having the following structure:

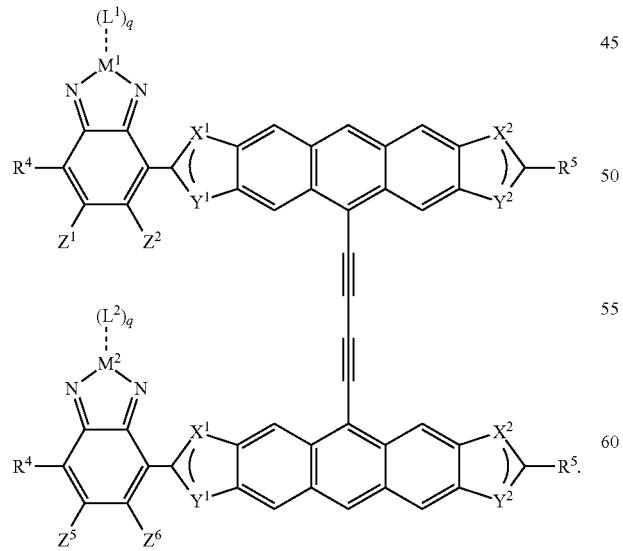

6. The compound of claim 1, wherein $L_1$, $L_2$, and $L_3$ are each individually Cl, Br, I, a linear, branched or cyclic aliphatic, aryl or heteroaryl group of up to 20 carbon atoms.

7. The compound of claim 1, wherein $M^1$ is S and $M^2$ is S, $M^1$ is S and $M^2$ is Se, or $M^1$ is S and $M^2$ is Te.

8. The compound of claim 1, wherein $M^1$ is Se and $M^2$ is Se or $M^1$ is Se and $M^2$ is Te.

9. The compound of claim 1, wherein $M^1$ is Te and $M^2$ is Te.

10. The compound of claim 1, wherein $Z^1$ and $Z^2$ or $Z^3$ and $Z^4$ or $Z^5$ and $Z^6$ are each N and are connected by a metal bridge atom to form, together with the carbon atoms to which they are attached, a 5 member ring system.

11. The compound of claim 10, wherein $Z^1$ and $Z^2$ are each N and are connected by a metal bridge atom to form, together with the carbon atoms to which they are attached, a 5 member ring system.

12. The compound of claim 11, having the following structure:

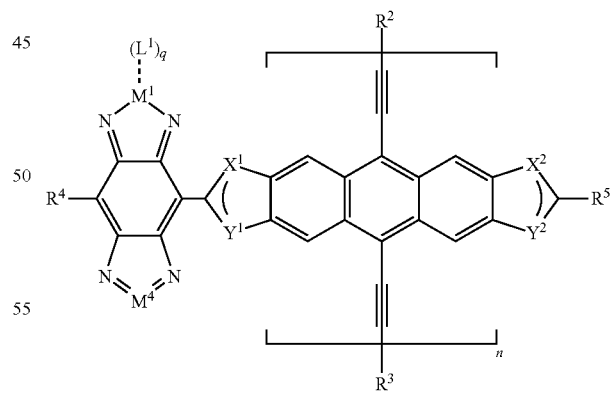

wherein $M^4$ is S, Se, or Te.

13. The compound of claim 3, having the following structure:

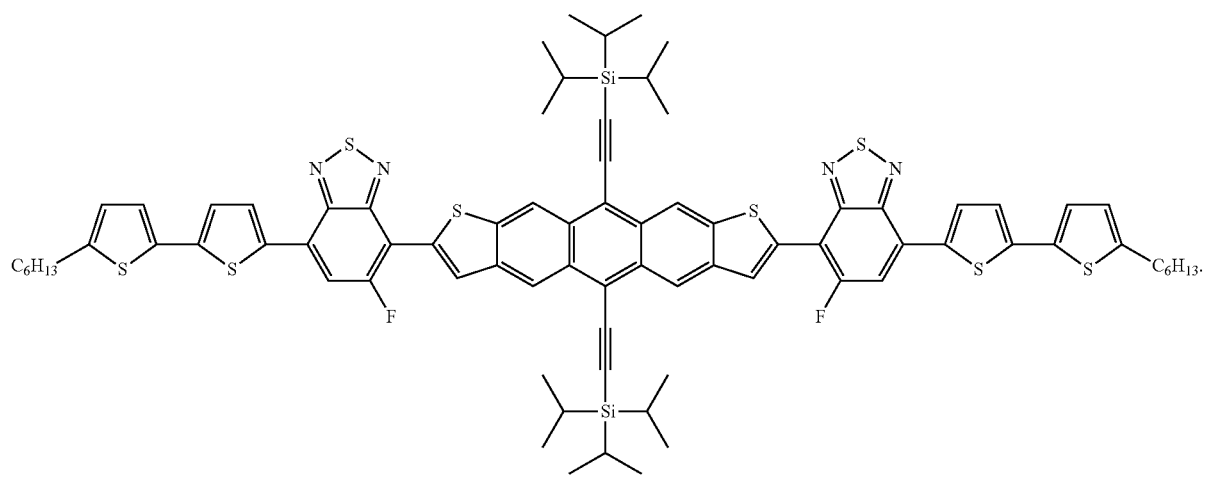

14. The compound of claim 3, having the following structure:

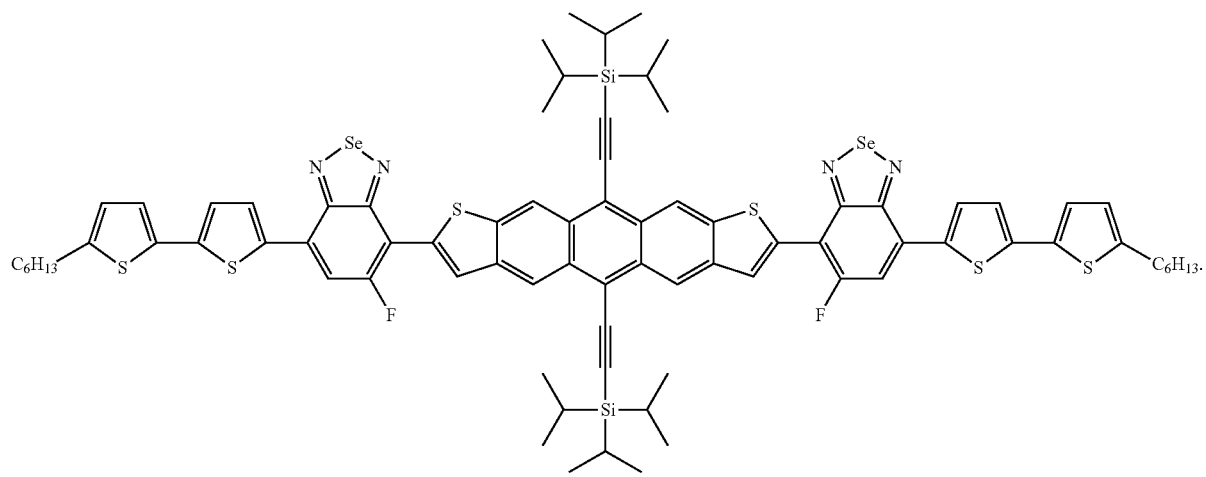

15. An electronic device comprising an organic or hybrid semiconducting or conducting layer or both comprising a compound of claim 1.

16. The electronic device of claim 15, wherein the semiconducting layer is photoactive.

17. The electronic device of claim 15, wherein the conducting layer is photoactive.

18. The electronic device of claim 15, wherein said device is a polymeric organic light-emitting diodes (PLED), a small-molecule organic light-emitting diodes (SM-OLED), an organic integrated circuit (O-ICs), an organic field effect transistor (OFET), an organic thin film transistor (OTFT), an organic solar cell (O-SC), or an organic laser diode (O-laser).

19. The electronic device of claim 15, wherein the electronic device comprises a single layer, a bi-layer, a multiple-layer stacking or a bulk heterojunction active layer.

20. A photovoltaic cell comprising an organic or hybrid semiconducting or conducting layer comprising a compound of claim 1.

21. A process for applying an organic or hybrid semiconducting or conducting layer on a substrate or an electrode, wherein the semiconducting or conducting layer comprises a compound of claim 1, the process comprising disposing said semiconducting or conducting layer on said substrate or said electrode.

* * * * *

UNITED STATES PATENT AND TRADEMARK OFFICE
CERTIFICATE OF CORRECTION

PATENT NO. : 9,444,060 B2
APPLICATION NO. : 14/781872
DATED : September 13, 2016
INVENTOR(S) : Al-Rafia et al.

It is certified that error appears in the above-identified patent and that said Letters Patent is hereby corrected as shown below:

In the Claims

Claim 1 on Column 36 Line 46, remove "X" and insert --E--.

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*